US007410970B2

(12) United States Patent
Janssens et al.

(10) Patent No.: US 7,410,970 B2
(45) Date of Patent: Aug. 12, 2008

(54) SUBSTITUTED 1,4,-DI-PIPERIDIN-4-YL-PIPERAZINE DERIVATIVES AND THEIR USE AS NEUROKININ ANTAGONISTS

(75) Inventors: Frans Eduard Janssens, Bonheide (BE); François Maria Sommen, Wortel (BE); Benoît Christian Albert Ghislain De Boeck, Genval (BE); Joseph Elisabeth Leenaerts, Rijkevorsel (BE); Yves Emiel Maria Van Roosbroeck, Hallaar (BE); Gaston Stanislas Marcella Diels, Ravels (BE)

(73) Assignee: Janssen Pharmaceutica, N.V., Beerse (BE)

( * ) Notice: Subject to any disclaimer, the term of this patent is extended or adjusted under 35 U.S.C. 154(b) by 369 days.

(21) Appl. No.: 10/527,821

(22) PCT Filed: Oct. 7, 2003

(86) PCT No.: PCT/EP03/50697

§ 371 (c)(1),
(2), (4) Date: Mar. 15, 2005

(87) PCT Pub. No.: WO2004/033428

PCT Pub. Date: Apr. 22, 2004

(65) Prior Publication Data

US 2006/0167008 A1  Jul. 27, 2006

(30) Foreign Application Priority Data

Oct. 8, 2002   (EP) .................................. 0211328
Dec. 23, 2002 (EP) .................................. 0214836

(51) Int. Cl.
*A61K 31/496* (2006.01)
*A61K 31/497* (2006.01)
*C07D 401/00* (2006.01)
*C07D 403/00* (2006.01)
*C07D 403/14* (2006.01)
*C07D 405/00* (2006.01)
*C07D 409/00* (2006.01)

(52) U.S. Cl. .................. 514/253.12; 544/360; 544/364
(58) Field of Classification Search ...................... None
See application file for complete search history.

(56) References Cited

U.S. PATENT DOCUMENTS

2006/0128271 A1* 6/2006 Janssens et al. ........ 514/253.12
2006/0252747 A1* 11/2006 Janssens et al. ............. 514/218

FOREIGN PATENT DOCUMENTS

WO        WO 97/16440 A1    5/1997

OTHER PUBLICATIONS

Smith et al. March's Advanced Organic Chemistry, 2001, 681-690.*
Jantzen and Robinson, Modern Pharmaceutics (editor Gilbert Banker), 1996, pp. 451 and 596.*
Giuseppe et al. Expert Opinion on Therapeutic Patents, 1997, 307-323.*
International Search Report for PCT/EP03/50697 date Feb. 10, 2004.

* cited by examiner

*Primary Examiner*—James O. Wilson
*Assistant Examiner*—Noble Jarrell
(74) *Attorney, Agent, or Firm*—woodcock Washburn LLP

(57) ABSTRACT

The invention concerns substituted 1,4-di-piperidin-4-yl-piperazine derivatives having neurokinin antagonistic activity, in particular $NK_1$ antagonistic activity, their preparation, compositions comprising them and their use as a medicine, in particular for the treatment of emesis, anxiety, depression, pain, pancreatitis and IBS.

20 Claims, No Drawings

SUBSTITUTED 1,4,-DI-PIPERIDIN-4-YL-PIPERAZINE DERIVATIVES AND THEIR USE AS NEUROKININ ANTAGONISTS

CROSS REFERENCE TO RELATED APPLICATIONS

This application is the national stage of Application No. PCT/EP2003/50697, filed Oct. 7, 2003, which application claims priority from PCT Patent Application No. PCT/EP02/11328 filed Oct. 8, 2002. and priority from PCT Patent Application No. PCT/EP02/14836 filed Dec. 23, 2002.

FIELD OF THE INVENTION

This invention concerns 1,4-di-piperidin-4-yl-piperazine derivatives having neurokinin antagonistic activity, in particular $NK_1$ antagonistic activity, their preparation, compositions comprising them and their use as a medicine, in particular for the treatment of emesis, anxiety, depression, pancreatitis and IBS.

BACKGROUND OF THE INVENTION

Neurokinins belong to a family of short peptides that are widely distributed in the mammalian central and peripheral nervous system (Bertrand and Geppetti, *Trends Pharmacol. Sci.* 17:255-259 (1996); Lundberg, *Can. J. Physiol. Pharmacol.* 73:908-914 (1995); Maggi, *Gen. Pharmacol* 26:911-944 (1995); Regoli et al., *Pharmacol. Rev.* 46 (1994)). They share the common C-terminal sequence Phe-Xaa-Gly-Leu-Met-$NH_2$. Neurokinins released from peripheral sensory nerve endings are believed to be involved in neurogenic inflammation. In the spinal cord/central nervous system, neurokinins may play a role in pain transmission/perception and in some autonomic reflexes and behaviours. The three major neurokinins are Substance P(SP), Neurokinin A ($NK_A$) and Neurokinin B ($NK_B$) with preferential affinity for three distinct receptor subtypes, termed $NK_1$, $NK_2$, and $NK_3$, respectively. However, functional studies on cloned receptors suggest strong functional cross-interaction between the 3 neurokinins and their corresponding receptors (Maggi and Schwartz, *Trends Pharmacol. Sci.* 18: 351-355 (1997)).

Species differences in structure of $NK_1$ receptors are responsible for species-related potency differences of $NK_1$ antagonists (Maggi, *Gen. Pharmacol.* 26:911-944 (1995); Regoli et al., *Pharmacol. Rev.* 46(4):551-599 (1994)). The human $NK_1$ receptor closely resembles the $NK_1$ receptor of guinea-pigs and gerbils but differs markedly from the $NK_1$ receptor of rodents. The development of neurokinin antagonists has led to date to a series of peptide compounds of which might be anticipated that they are metabolically too labile to be employed as pharmaceutically active substances (Longmore J. et al., *DN&P* 8(1):5-23 (1995)).

The neurokinins are involved in emesis, (stress-related) anxiety states, inflammatory responses, smooth muscle contraction and pain perception. Neurokinin antagonists are in development for indications such as emesis, anxiety and depression, irritable bowel syndrome (IBS), circadian rhythm disturbances, visceral pain, neurogenic inflammation, asthma, micturition disorders, and nociception.

Emesis

Nausea and vomiting are among the most distressing side effects of cancer chemotherapy. These reduce the quality of life and may cause patients to delay or refuse, potentially curative drugs (Kris et al., *J. Clin. Oncol.*, 3:1379-1384 (1985)). The incidence, intensity and pattern of emesis are determined by different factors, such as the chemotherapeutic agent, dosage and route of administration. Typically, early or acute emesis starts within the first 4 h after chemotherapy administration, reaching a peak between 4 h and 10 h, and decreases by 12 to 24 h. Delayed emesis (developing after 24 h and continuing until 3-5 days post chemotherapy) is observed with most 'high-emetogenic' chemotherapeutic drugs (level 4 and 5 according to Hesketh et al., *J. Clin. Oncol.* 15:103 (1997)). In humans, these 'high-emetogenic' anti-cancer treatments, including cis-platinum, induce acute emesis in >98% and delayed emesis in 60-90% of cancer patients.

Animal models of chemotherapy such as cisplatin-induced emesis in ferrets (Rudd and Naylor, Neuropharmacology 33:1607-1608 (1994); Naylor and Rudd, *Cancer. Surv.* 21:117-135 (1996)) have successfully predicted the clinical efficacy of the 5-$HT_3$ receptor antagonists. Although this discovery led to a successful therapy for the treatment of chemotherapy- and radiation-induced sickness in cancer patients, 5-$HT_3$ antagonists such as ondansetron and granisetron (either or not associated with dexamethasone) are effective in the control of the acute emetic phase (the first 24 h) but can only reduce the development of delayed emesis (>24 h) with poor efficacy (De Mulder et al., *Annuals of Internal Medicine* 113:834-840 (1990); Roila, *Oncology* 50:163-167 (1993)). Despite these currently most effective treatments for the prevention of both acute and delayed emesis, still 50% of patients suffer from delayed vomiting and/or nausea (Antiemetic Subcommittee, *Annals Oncol.* 9:811-819 (1998)).

In contrast to 5-$HT_3$ antagonists, $NK_1$ antagonists such as CP-99,994 (Piedimonte et al., *L. Pharmacol. Exp. Ther.* 266: 270-273 (1993)) and aprepitant (also known as MK-869 or L-754,030; Kramer et al., *Science* 281:1640-1645 (1998); Rupniak and Kramer, *Trends Pharmacol. Sci.* 20:1-12 (1999)) have now been shown to inhibit not only the acute but also the delayed phase of cisplatin-induced emesis in animals (Rudd et al., *Br. J. Pharmacol.* 119:931-936 (1996); Tattersall et al., *Neuropharmacology* 39:652-663 (2000)). $NK_1$ antagonists have also been demonstrated to reduce 'delayed' emesis in man in the absence of concomitant therapy (Cocquyt et al., *Eur. J. Cancer* 37:835-842 (2001); Navari et al. *N. Engl. L. Med.* 340:190-195 (1999)). When administered together with dexamethasone and 5-$HT_3$ antagonists, moreover, $NK_1$ antagonists (such as MK-869 and CJ-11,974, also known as Ezlopitant) have been shown to produce additional effects in the prevention of acute emesis (Campos et al., *J. Clin. Oncol.* 19:1759-1767 (2001); Hesketh et al., *Clin. Oncol.* 17:338-343 (1999)).

Central neurokinin $NK_1$ receptors play a major role in the regulation of emesis. $NK_1$ antagonists are active against a wide variety of emetic stimuli (Watson et al., *Br. J. Pharmacol.* 115:84-94 (1995); Tattersall et al., *Neuropharmacol.* 35:1121-1129 (1996); Megens et al., *J. Pharmacol. Exp. Ther.* 1-14 (2002)). The compounds are suggested to act by blocking central $NK_1$-receptors in the nucleus tractus solitarius. Apart from $NK_1$ antagonism, CNS penetration is thus a prerequisite for the antiemetic activity of these compounds. Loperamide-induced emesis in ferrets can be used as a fast and reliable screening model for the antiemetic activity of $NK_1$ antagonists. Further evaluation of their therapeutic value in the treatment of both the acute and the delayed phases of cisplatin-induced emesis has been demonstrated in the established ferret model (Rudd et al., *Br. J. Pharmacol.* 119:931-936 (1994)). This model studies both 'acute' and 'delayed' emesis after cisplatin and has been validated in terms of its sensitivity to 5-$HT_3$ receptor antagonists, glucocorticoids (Sam et al., *Eur. J. Pharmacol.* 417:231-237 (2001)) and other pharmacological challenges. It is unlikely that any future anti-emetic would find clinical acceptance unless successfully treating both the 'acute' and 'delayed' phases of emesis.

Depression and Anxiety

Depression is one of the most common affective disorders of modern society with a high and still increasing prevalence, particularly in the younger members of the population. The life time prevalence rates of Major depression (MDD, DSM-IV) is currently estimated to be 10-25% for women and 5-12% for men, whereby in about 25% of patients the life time MDD is recurrent, without full inter-episode recovery and superimposed on dysthymic disorder. There is a high co-morbidity of depression with other mental disorders and, particularly in younger population high association with drug and alcohol abuse. In the view of the fact that depression primarily affects the population between 18-44 years of age e.g. the most productive population, it is obvious that it imposes a high burden on individuals, families and the whole society.

Among all therapeutic possibilities, the therapy with anti-depressants is incontestably the most effective. A large number of antidepressants have been developed and introduced to the market in the course of the last 40 years. Nevertheless, none of the current antidepressants fulfill all criteria of an ideal drug (high therapeutic and prophylactic efficacy, rapid onset of action, completely satisfactory short- and long-term safety, simple and favorable pharmacokinetics) or is without side effects which in one or the other way limits their use in all groups and subgroups of depressed patients.

Since no treatment of the cause of depression exists at present, nor appears imminent, and no antidepressant is effective in more than 60-70% of patients; the development of a new antidepressant which may circumvent any of the disadvantages of the available drugs is justified.

Several findings indicate involvement of SP in stress-related anxiety states. Central injection of SP induces a cardiovascular response resembling the classical "fight or flight" reaction characterized physiologically by vascular dilatation in skeletal muscles and decrease of mesenteric and renal blood flow. This cardiovascular reaction is accompanied by a behavioral response observed in rodents after noxious stimuli or stress (Culman and Unger, *Can. J. Physiol. Pharmacol.* 73:885-891 (1995)). In mice, centrally administered $NK_1$ agonists and antagonists are anxiogenic and anxiolytic, respectively (Teixeira et al., *Eur. J. Pharmacol.* 311:7-14 (1996)). The ability of $NK_1$ antagonists to inhibit thumping induced by SP (or by electric shock; Ballard et al., *Trends Pharmacol. Sci.* 17:255-259 (2001)) might correspond to this antidepressant/anxiolytic activity, since in gerbils thumping plays a role as an alerting or warning signal to conspecifics.

The $NK_1$ receptor is widely distributed throughout the limbic system and fear-processing pathways of the brain, including the amygdala, hippocampus, septum, hypothalamus, and periaqueductal grey. Additionally, substance P is released centrally in response to traumatic or noxious stimuli and substance P-associated neurotransmission may contribute to or be involved in anxiety, fear, and the emotional disturbances that accompany affective disorders such as depression and anxiety. In support of this view, changes in substance P content in discrete brain regions can be observed in response to stressful stimuli (Brodin et al., *Neuropeptides* 26:253-260 (1994)).

Central injection of substance P mimetics (agonists) induces a range of defensive behavioral and cardiovascular alterations including conditioned place aversion (Elliott, *Exp. Brain. Res.* 73:354-356 (1988)), potentiated acoustic startle response (Krase et al., *Behav. Brain. Res.* 63:81-88 (1994)), distress vocalizations, escape behavior (Kramer et al., *Science* 281:1640-1645 (1998)) and anxiety on the elevated plus maze (Aguiar and Brandao, *Physiol. Behav.* 60:1183-1186 (1996)). These compounds did not modify motor performance and co-ordination on the rotarod apparatus or ambulation in an activity cage. Down-regulation of substance P biosynthesis occurs in response to the administration of known anxiolytic and antidepressant drugs (Brodin et al., *Neuropeptides* 26:253-260 (1994); Shirayama et al., *Brain. Res.* 739:70-78 (1996)). Similarly, a centrally administered $NK_1$ agonist-induced vocalization response in guinea-pigs can be antagonized by antidepressants such as imipramine and fluoxetine as well as L-733,060, an $NK_1$ antagonist. These studies provide evidence suggesting that blockade of central $NK_1$ receptors may inhibit psychological stress in a manner resembling antidepressants and anxiolytics (Rupniak and Kramer, *Trends Pharmacol. Sci.* 20:1-12 (1999)), but without the side effects of present medications. This is supported by data demonstrating that aprepitant is a clinically efficacious antidepressant with significant anxiolytic activity in a randomized double-blind placebo-controlled study (Kramer et al., *Science* 281:1640-1645 (1998)).

Irritable Bowel Syndrome (IBS)

Patients with irritable bowel syndrome (IBS) experience impaired quality of life, and utilize health care resources extensively as they seek better "solutions" (including unnecessary repeated investigations or even surgery). Although these patients suffer from a 'benign' disorder (in other words, they will never die or develop significant complications), they nevertheless cause a significant economic burden by extensive health care resource utilization, and absence from work.

A reasonable number of pre-clinical publications over the role of $NK_1$ receptors in visceral pain has been published. Using $NK_1$ receptor knockout mice and $NK_1$ antagonists in animal models, different groups have demonstrated the important role played by the $NK_1$ receptor in hyperalgesia and visceral pain. The distribution of $NK_1$ receptors and substance P favors a major role in visceral rather than in somatic pain. Indeed more than 80% of visceral primary afferent contain substance P compared with only 25% skin afferents. $NK_1$ receptors are also involved in gastrointestinal motility (Tonini et al., *Gastroenterol.* 120:938-945 (2001); Okano et al., *J. Pharmacol. Exp. Ther.* 298:559-564 (2001)). Because of this dual role in both gastrointestinal motility and in nociception, $NK_1$ antagonists are considered to have potential to ameliorate symptoms in IBS patients.

Pancreatitis

It has been suggested that substance-P, as one of two main neuropeptides involved in neurogenic inflammation acting via the $NK_1$ receptor, plays an important proinflammatory role in regulating the severity of acute pancreatitis and pancreatitis-associated lung injury. Impaired long function in severe acute pancreatitis is the primary cause of morbidity and mortality in this condition. This has been clearly demonstrated using $NK_1^{-/-}$ mice (Bhatia et al., *Proceedings of the National Academy of Sciences of the USA* 95(8):4760-4765 (1998)). Also, it has been shown that preprotachykinin-A gene deletion protects mice against acute pancreatitis (Bhatia et al., *American J. of Physiology* 284(5):G380-G386(2003)). Furthermore, several studies have been published indicating that $NK_1$-antagonists (e.g. CP-96 345 and CP-99 994) may play a role in treating pancreatitis, e.g. in influencing the intensity, duration and frequency of pain in chronic pancreatitis patients (Maa et al., *American J. of Physiology* 279: G726-G732 (2000); Grady et al., *British J. of Pharmacology* 130(3):505-512 (2000); Vera-Portocarrero et al., *Anesthesiology* 98(2):474-484 (2003) and Shrikhande et al., *Pain* 91(3):209-217 (2001)).

2. Background Prior Art

Compounds containing the 1-piperidin-4-yl-piperazinyl moiety were published in WO 97/16440-A1, published May 9, 1997 by Janssen Pharmaceutica N.V. for use as substance P antagonists, in WO 02/32867, published Apr. 25, 2002 by Glaxo Group Ltd. for their special advantages as neurokinin antagonists (more specifically were disclosed 4-piperazin-1-yl-piperidine-1-carboxylic acid amide derivatives), in WO 01/30348-A1, published May 3, 2001 by Janssen Pharmaceutica N.V., for use as substance P antagonists for influencing the circadian timing system, and in WO 02/062784-A1, published Aug. 15, 2002 by Hoffmann-La Roche AG for use as neurokinin 1 antagonists.

The compounds of the present invention differ from the compounds of the prior art in the substitution of the piperazinyl moiety, being a substituted piperidinyl moiety as well as in their improved ability as potent, orally and centrally active neurokinin antagonists with therapeutic value, especially for the treatment of emesis, anxiety and depression, irritable bowel syndrome (IBS), circadian rhythm disturbances, visceral pain, neurogenic inflammation, asthma, micturition disorders, and nociception.

DESCRIPTION OF THE INVENTION

The present invention relates to novel 1,4-di-piperidin-4-yl-piperazine derivatives according to the general Formula (I)

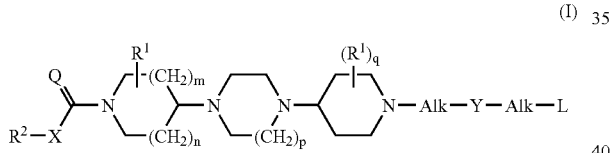

(I)

the pharmaceutically acceptable acid or base addition salts thereof, the stereochemically isomeric forms thereof, the N-oxide form thereof and prodrugs thereof, wherein:

n is an integer, equal to 0, 1 or 2;

m is an integer, equal to 1 or 2, provided that if m is 2, then n is 1;

p is an integer equal to 1 or 2;

Q is O or $NR^3$;

X is a covalent bond or a bivalent radical of formula —O—, —S— or —$NR^3$—;

each $R^3$ independently from each other, is hydrogen or alkyl;

each $R^1$ independently from each other, is selected from the group of $Ar^1$, $Ar^1$-alkyl and di($Ar^1$)-alkyl;

q is an integer equal to 0 or 1;

$R^2$ is alkyl, $Ar^2$, $Ar^2$-alkyl, $Het^1$ or $Het^1$-alkyl;

Y is a covalent bond or a bivalent radical of formula —C(=O)— or —$SO_2$—;

each Alk represents, independently from each other, a covalent bond; a bivalent straight or branched, saturated or unsaturated hydrocarbon radical having from 1 to 6 carbon atoms; or a cyclic saturated or unsaturated hydrocarbon radical having from 3 to 6 carbon atoms; each radical optionally substituted on one or more carbon atoms with one or more alkyl, phenyl, halo, cyano, hydroxy, formyl and amino radicals;

L is selected from the group of hydrogen, alkyloxy, $Ar^3$-oxy, alkyloxycarbonyl, mono- and di(alkyl)amino, mono- and di($Ar^3$)amino, mono- and di(alkyloxycarbonyl)amino, $Ar^3$, $Ar^3$-carbonyl, $Het^2$ and $Het^2$-carbonyl;

$Ar^1$ is phenyl, optionally substituted with 1, 2 or 3 substituents each independently from each other selected from the group of halo, alkyl, cyano, aminocarbonyl and alkyloxy;

$Ar^2$ is naphthalenyl or phenyl, each optionally substituted with 1, 2 or 3 substituents, each independently from each other, selected from the group of halo, nitro, amino, mono- and di(alkyl)amino, cyano, alkyl, hydroxy, alkyloxy, carboxyl, alkyloxycarbonyl, aminocarbonyl and mono- and di(alkyl)aminocarbonyl;

$Ar^3$ is naphthalenyl or phenyl, optionally substituted with 1, 2 or 3 substituents each independently from each other selected from the group of alkyloxy, alkyl, halo, hydroxy, pyridinyl, morpholinyl, pyrrolidinyl, imidazo[1,2-α]pyridinyl, morpholinylcarbonyl, pyrrolidinylcarbonyl, amino and cyano;

$Het^1$ is a monocyclic heterocyclic radical selected from the group of pyrrolyl, pyrazolyl, imidazolyl, furanyl, thienyl, oxazolyl, isoxazolyl, thiazolyl, thiadiazolyl, isothiazolyl, pyridinyl, pyrimidinyl, pyrazinyl and pyridazinyl; or a bicyclic heterocyclic radical selected from the group of quinolinyl, quinoxalinyl, indolyl, benzimidazolyl, benzoxazolyl, benzisoxazolyl, benzothiazolyl, benzisothiazolyl, benzofuranyl and benzothienyl; each heterocyclic radical may optionally be substituted on any atom by a radical selected from the group of halo and alkyl;

$Het^2$ is a monocyclic heterocyclic radical selected from the group of pyrrolidinyl, dioxolyl, imidazolidinyl, pyrrazolidinyl, piperidinyl, morpholinyl, dithianyl, thiomorpholinyl, piperazinyl, imidazolidinyl, tetrahydrofuranyl, 2H-pyrrolyl, pyrrolinyl, imidazolinyl, pyrrazolinyl, pyrrolyl, imidazolyl, pyrazolyl, triazolyl, furanyl, thienyl, oxazolyl, isoxazolyl, thiazolyl, thiadiazolyl, isothiazolyl, pyridinyl, pyrimidinyl, pyrazinyl, pyridazinyl and triazinyl; or a bicyclic heterocyclic radical selected from the group of benzopiperidinyl, quinolinyl, quinoxalinyl, indolyl, isoindolyl, chromenyl, benzimidazolyl, imidazo[1,2-α]pyridinyl, benzoxazolyl, benzisoxazolyl, benzothiazolyl, benzisothiazolyl, benzofuranyl and benzothienyl; each radical optionally substituted with one or more radicals selected from the group of $Ar^1$, $Ar^1$alkyl, halo, hydroxy, alkyl, piperidinyl, pyrrolyl, thienyl, oxo, alkyloxy, alkyloxyalkyl and alkyloxycarbonyl; and alkyl is a straight or branched saturated hydrocarbon radical having from 1 to 6 carbon atoms or a cyclic saturated hydrocarbon radicals having from 3 to 6 carbon atoms; optionally substituted on one or more carbon atoms with one or more radicals selected from the group of phenyl, halo, cyano, oxo, hydroxy, formyl and amino radicals.

More in particular, the invention relates to a compound according to the general Formula (I), the pharmaceutically acceptable acid or base addition salts thereof, the stereochemically isomeric forms thereof, the N-oxide form thereof and a prodrug thereof, wherein:

n is 1;

m is 1;

p is 1;

Q is O;

X is a covalent bond;

each $R^1$ is $Ar^1$ or $Ar^1$-alkyl;

q is 0 or 1;

$R^2$ is $Ar^2$;

Y is a covalent bond or a bivalent radical of formula —C(=O)— or —$SO_2$—;

each Alk represents, independently from each other, a covalent bond; a bivalent straight or branched, saturated or unsaturated hydrocarbon radical having from 1 to 6 carbon atoms; or a cyclic saturated or unsaturated hydrocarbon radical having from 3 to 6 carbon atoms; each radical optionally substituted on one or more carbon atoms with one or more phenyl, halo, cyano, hydroxy, formyl and amino radicals;

L is selected from the group of hydrogen, alkyloxy, $Ar^3$-oxy, alkyloxy-carbonyl, mono- and di(alkyl)amino, mono- and di($Ar^3$)amino, $Ar^3$ and $Het^2$;

$Ar^1$ is phenyl, optionally substituted with 1, 2 or 3 alkyl radicals;

$Ar^2$ is phenyl, optionally substituted with 1, 2 or 3 alkyl radicals;

$Ar^3$ is phenyl, optionally substituted with 1, 2 or 3 substituents each independently from each other selected from the group of alkyloxy, alkyl, halo, hydroxy, pyridinyl, morpholinyl, pyrrolidinyl, imidazo[1,2-α]pyridinyl, morpholinylcarbonyl, pyrrolidinylcarbonyl, amino and cyano;

$Het^2$ is a monocyclic heterocyclic radical selected from the group of pyrrolidinyl, piperidinyl, morpholinyl, pyrrolyl, imidazolyl, pyrazolyl, furanyl, thienyl, isoxazolyl, thiazolyl, thiadiazolyl, pyridinyl, pyrimidinyl, pyrazinyl, and pyridazinyl; or a bicyclic heterocyclic radical selected from the group of benzopiperidinyl, quinolinyl, quinoxalinyl, indolyl, chromenyl and benzimidazolyl; each radical optionally substituted with one or more radicals selected from the group of $Ar^1$, $Ar^1$alkyl, halo, hydroxy, alkyl, piperidinyl, pyrrolyl, thienyl, oxo and alkyloxycarbonyl; and alkyl is a straight hydrocarbon radical having 1 to 6 carbon atoms, optionally substituted with one or more halo radicals;

More in particular, the invention relates to a compound according to the general Formula (I), the pharmaceutically acceptable acid or base addition salts thereof, the stereochemically isomeric forms thereof, the N-oxide form thereof and a prodrug thereof, wherein $R^1$ is $Ar^1$methyl and attached to the 2-position or $R^1$ is $Ar^1$ and attached to the 3-position, as exemplified in either of the following formulas for compounds according to Formula (I) wherein m and n are equal to 1 and Ar is an unsubstituted phenyl. Preferably, $Ar^1$methyl is an unsubstituted benzyl radical.

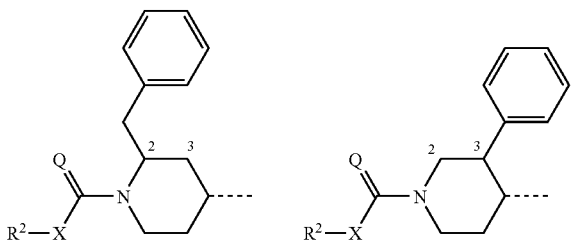

More in particular, the invention relates to a compound according to the general Formula (I), the pharmaceutically acceptable acid or base addition salts thereof, the stereochemically isomeric forms thereof, the N-oxide form thereof and a prodrug thereof, wherein the $R^2$—X—C(=Q)- moiety is 3,5-di-(trifluoromethyl)phenylcarbonyl.

In the framework of this application, alkyl is defined as a monovalent straight or branched saturated hydrocarbon radical having from 1 to 6 carbon atoms, for example methyl, ethyl, propyl, butyl, 1-methylpropyl, 1,1-dimethylethyl, pentyl, hexyl; alkyl further defines a monovalent cyclic saturated hydrocarbon radical having from 3 to 6 carbon atoms, for example cyclopropyl, methylcyclopropyl, cyclobutyl, cyclopentyl and cyclohexyl. The definition of alkyl also comprises an alkyl radical that is optionally substituted on one or more carbon atoms with one or more phenyl, halo, cyano, oxo, hydroxy, formyl and amino radicals, for example hydroxyalkyl, in particular hydroxymethyl and hydroxyethyl and polyhaloalkyl, in particular difluoromethyl and trifluoromethyl.

In the framework of this application, halo is generic to fluoro, chloro, bromo and iodo.

In the framework of this application, with "compounds according to the invention" is meant a compound according to the general Formula (I), the pharmaceutically acceptable acid or base addition salts thereof, the stereochemically isomeric forms thereof, the N-oxide form thereof and a prodrug thereof.

In the framework of this application, especially in the moiety $Alk^a$-Y-$Alk^b$ in Formula (I), when two or more consecutive elements of said moiety denote a covalent bond, then a single covalent bond is denoted. For example, when $Alk^a$ and Y denote both a covalent bond and $Alk^b$ is —$CH_2$—, then the moiety $Alk^a$-Y-$Alk^b$ denotes —$CH_2$—.

The pharmaceutically acceptable salts are defined to comprise the therapeutically active non-toxic acid addition salts forms that the compounds according to Formula (I) are able to form. Said salts can be obtained by treating the base form of the compounds according to Formula (I) with appropriate acids, for example inorganic acids, for example hydrohalic acid, in particular hydrochloric acid, hydrobromic acid, sulfuric acid, nitric acid and phosphoric acid; organic acids, for example acetic acid, hydroxyacetic acid, propanoic acid, lactic acid, pyruvic acid, oxalic acid, malonic acid, succinic acid, maleic acid, fumaric acid, malic acid, tartaric acid, citric acid, methanesulfonic acid, ethanesulfonic acid, benzenesulfonic acid, p-toluenesulfonic acid, cyclamic acid, salicylic acid, p-aminosalicylic acid and pamoic acid. Particularly preferred is fumaric acid.

The compounds according to Formula (I) containing acidic protons may also be converted into their therapeutically active non-toxic metal or amine addition salts forms by treatment with appropriate organic and inorganic bases. Appropriate base salts forms comprise, for example, the ammonium salts, the alkaline and earth alkaline metal salts, in particular lithium, sodium, potassium, magnesium and calcium salts, salts with organic bases, e.g. the benzathine, N-methyl-D-glucamine, hybramine salts, and salts with amino acids, for example arginine and lysine.

Conversely, said salts forms can be converted into the free forms by treatment with an appropriate base or acid.

The term addition salt as used in the framework of this application also comprises the solvates that the compounds according to Formula (I) as well as the salts thereof, are able to form. Such solvates are, for example, hydrates and alcoholates.

The N-oxide forms of the compounds according to Formula (I) are meant to comprise those compounds of Formula (I) wherein one or several nitrogen atoms are oxidized to the so-called N-oxide, particularly those N-oxides wherein one or more tertiary nitrogens (e.g of the piperazinyl or piperidinyl radical) are N-oxidized. Such N-oxides can easily be obtained by a skilled person without any inventive skills and they are obvious alternatives for the compounds according to Formula (I) since these compounds are metabolites, which are formed by oxidation in the human body upon uptake. As is generally known, oxidation is normally the first step involved in drug metabolism (Textbook of Organic Medicinal and Pharmaceutical Chemistry, 1977, pages 70-75). As is also generally known, the metabolite form of a compound can also be administered to a human instead of the compound per se, with much the same effects.

The compounds according to the invention possess at least 2 oxydizable nitrogens (tertiary amines moieties). It is therefore highly likely that N-oxides are to form in the human metabolism.

The compounds of Formula (I) may be converted to the corresponding N-oxide forms following art-known procedures for converting a trivalent nitrogen into its N-oxide form. Said N-oxidation reaction may generally be carried out by reacting the starting material of Formula (I) with an appropriate organic or inorganic peroxide. Appropriate inorganic peroxides comprise, for example, hydrogen peroxide, alkali metal or earth alkaline metal peroxides, e.g. sodium peroxide, potassium peroxide; appropriate organic peroxides may comprise peroxy acids such as, for example, benzenecarboperoxoic acid or halo substituted benzenecarboperoxoic acid, e.g. 3-chlorobenzenecarboperoxoic acid, peroxoalkanoic acids, e.g. peroxoacetic acid, alkylhydroperoxides, e.g. tert-butyl hydroperoxide. Suitable solvents are, for example, water, lower alkanols, e.g. ethanol and the like, hydrocarbons, e.g. toluene, ketones, e.g. 2-butanone, halogenated hydrocarbons, e.g. dichloromethane, and mixtures of such solvents.

The term "stereochemically isomeric forms" as used hereinbefore defines all the possible isomeric forms that the compounds of Formula (I) may possess. Unless otherwise mentioned or indicated, the chemical designation of compounds denotes the mixture of all possible stereochemically isomeric forms, said mixtures containing all diastereomers and enantiomers of the basic molecular structure. More in particular, stereogenic centers may have the R- or S-configuration; substituents on bivalent cyclic (partially) saturated radicals may have either the cis- or trans-configuration. Compounds encompassing double bonds can have an E or Z-stereochemistry at said double bond. Stereochemically isomeric forms of the compounds of Formula (I) are obviously intended to be embraced within the scope of this invention.

Following CAS nomenclature conventions, when two stereogenic centers of known absolute configuration are present in a molecule, an R or S descriptor is assigned (based on Cahn-Ingold-Prelog sequence rule) to the lowest-numbered chiral center, the reference center. The configuration of the second stereogenic center is indicated using relative descriptors [R*,R*] or [R*,S*], where R* is always specified as the reference center and [R*,R*] indicates centers with the same chirality and [R*,S*] indicates centers of unlike chirality. For example, if the lowest-numbered chiral center in the molecule has an S configuration and the second center is R, the stereo descriptor would be specified as S-[R*,S*]. If "α" and "β" are used: the position of the highest priority substituent on the asymmetric carbon atom in the ring system having the lowest ring number, is arbitrarily always in the "α" position of the mean plane determined by the ring system. The position of the highest priority substituent on the other asymmetric carbon atom in the ring system (hydrogen atom in compounds according to Formula (I)) relative to the position of the highest priority substituent on the reference atom is denominated "α", if it is on the same side of the mean plane determined by the ring system, or "β", if it is on the other side of the mean plane determined by the ring system.

Compounds according to Formula (I) and some of the intermediate compounds have at least two stereogenic centers in their structure, namely at the 2-position of the piperidinyl-moiety (R or S) and at the 4-position, where the attached radical may be either in the cis or trans position with respect to the radical at the 2-position on the piperidinyl-moiety.

The invention also comprises derivative compounds (usually called "pro-drugs") of the pharmacologically-active compounds according to the invention, which are degraded in vivo to yield the compounds according to the invention. Pro-drugs are usually (but not always) of lower potency at the target receptor than the compounds to which they are degraded. Pro-drugs are particularly useful when the desired compound has chemical or physical properties that make its administration difficult or inefficient. For example, the desired compound may be only poorly soluble, it may be poorly transported across the mucosal epithelium, or it may have an undesirably short plasma half-life. Further discussion on pro-drugs may be found in Stella, V. J. et al., "Prodrugs", *Drug Delivery Systems,* 1985, pp. 112-176, and *Drugs,* 1985, 29, pp. 455-473.

Pro-drugs forms of the pharmacologically-active compounds according to the invention will generally be compounds according to Formula (I), the pharmaceutically acceptable acid or base addition salts thereof, the stereochemically isomeric forms thereof and the N-oxide form thereof, having an acid group which is esterified or amidated. Included in such esterified acid groups are groups of the formula —COOR$^x$, where R$^x$ is a C$_{1-6}$alkyl, phenyl, benzyl or one of the following groups:

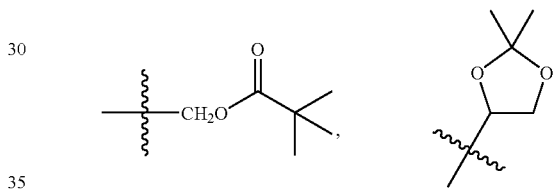

Amidated groups include groups of the formula —CONR$^y$R$^z$, wherein R$^y$ is H, C$_{1-6}$alkyl, phenyl or benzyl and R$^z$ is —OH, H, C$_{1-6}$alkyl, phenyl or benzyl. Compounds according to the invention having an amino group may be derivatised with a ketone or an aldehyde such as formaldehyde to form a Mannich base. This base will hydrolyze with first order kinetics in aqueous solution.

The compounds of Formula (I) as prepared in the processes described below may be synthesized in the form of racemic mixtures of enantiomers that can be separated from one another following art-known resolution procedures. The racemic compounds of Formula (I) may be converted into the corresponding diastereomeric salt forms by reaction with a suitable chiral acid. Said diastereomeric salt forms are subsequently separated, for example, by selective or fractional crystallization and the enantiomers are liberated therefrom by alkali. An alternative manner of separating the enantiomeric forms of the compounds of Formula (I) involves liquid chromatography using a chiral stationary phase. Said pure stereochemically isomeric forms may also be derived from the corresponding pure stereochemically isomeric forms of the appropriate starting materials, provided that the reaction occurs stereospecifically. Preferably if a specific stereoisomer is desired, said compound would be synthesized by stereospecific methods of preparation. These methods will advantageously employ enantiomerically pure starting materials.

Pharmacology

Substance P and other neurokinins are involved in a variety of biological actions such as pain transmission (nociception), neurogenic inflammation, smooth muscle contraction, plasma protein extravasation, vasodilation, secretion, mast cell degranulation, and also in activation of the immune system. A number of diseases are deemed to be engendered by activation of neurokinin receptors, in particular the $NK_1$ receptor, by excessive release of substance P and other neurokinins in particular cells such as cells in the neuronal plexi of the gastrointestinal tract, unmyelinated primary sensory afferent neurons, sympathetic and parasympathetic neurons and nonneuronal cell types (DN&P 8(1):5-23 (1995) and Longmore J. et al., "Neurokinin Receptors" *Pharmacological Reviews* 46(4):551-599 (1994)).

The compounds of the present invention are potent inhibitors of neurokinin-mediated effects, in particular those mediated via the $NK_1$ receptor, and may therefore be described as neurokinin antagonists or tachykinin antagonists, especially as substance P antagonists, as indicated in vitro by the antagonism of substance P-induced relaxation of pig coronary arteries which is described hereinafter. The binding affinity of the present compounds for the human, guinea-pig and gerbil neurokinin receptors may be determined in vitro in a receptor binding test using $^3$H-substance-P as radioligand. The subject compounds also show substance-P antagonistic activity in vivo as may be evidenced by, for instance, the antagonism of substance P-induced plasma extravasation in guinea-pigs, or the antagonism of drug-induced emesis in ferrets (Watson et al., *Br. J. Pharmacol.* 115:84-94 (1995)).

In view of their capability to antagonize the actions of neurokinins by blocking the neurokinin receptors, and in particular antagonizing the actions of substance P by blocking the $NK_1$ receptor, the compounds according to the invention are useful as a medicine, in particular in the prophylactic and therapeutic treatment of neurokinin-mediated conditions.

The invention therefore relates to a compound according to the general Formula (I), the pharmaceutically acceptable acid or base addition salts thereof, the stereochemically isomeric forms thereof, the N-oxide form thereof and prodrugs thereof, for use as a medicine.

The invention also relates to the use of a compound according to any one of claims 1-3 for the manufacture of a medicament for treating, either prophylactic or therapeutic or both, neurokinin mediated conditions.

The compounds according to the invention are useful in the treatment of CNS disorders, in particular depression, anxiety disorders, stress-related disorders, sleep disorders, cognitive disorders, personality disorders, schizoaffective disorders, eating disorders, neurodegenerative diseases, addiction disorders, mood disorders, sexual dysfunction, pain and other CNS-related conditions; inflammation; allergic disorders; emesis; gastrointestinal disorders, in particular irritable bowel syndrome (IBS); skin disorders; vasospastic diseases; fibrosing and collagen diseases; disorders related to immune enhancement or suppression and rheumatic diseases and body weight control.

In particular, the compounds according to the invention are useful in the treatment or prevention of depression including but not limited to major depressive disorders including bipolar depression; unipolar depression; single or recurrent major depressive episodes with or without psychotic features, catatonic features, melancholic features, atypical features or post-partum onset, and, in the case of recurrent episodes, with or without seasonal pattern. Other mood disorders encompassed within the term "major depressive disorder" include dysthymic disorder with early or late onset and with or without atypical features, bipolar I disorder, bipolar II disorder, cyclothymic disorder, recurrent brief depressive disorder, mixed affective disorder, neurotic depression, post traumatic stress disorder and social phobia; dementia of the Alzheimer's type with early or late onset, with depressed mood; vascular dementia with depressed mood; substance-induced mood disorders such as mood disorders induced by alcohol, amphetamines, cocaine, hallucinogens, inhalants, opioids, phencyclidine, sedatives, hypnotics, anxiolytics and other substances; schizoaffective disorder of the depressed type; and adjustment disorder with depressed mood. Major depressive disorders may also result from a general medical condition including, but not limited to, myocardial infarction, diabetes, miscarriage or abortion, etc.

In particular, the compounds according to the invention are useful in the treatment or prevention of anxiety disorders, including but not limited to panic attack; agoraphobia; panic disorder without agoraphobia; agoraphobia without history of panic disorder; specific phobia; social phobia; obsessive-compulsive disorder; post-traumatic stress disorder; acute stress disorder; generalized anxiety disorder; anxiety disorder due to a general medical condition; substance-induced anxiety disorder; and anxiety disorder not otherwise specified.

In particular, the compounds according to the invention are useful in the treatment or prevention of stress-related disorders associated with depression and/or anxiety, including but not limited to acute stress reaction; adjustment disorders, such as brief depressive reaction, prolonged depressive reaction, mixed anxiety and depressive reaction, adjustment disorder with predominant disturbance of other emotions, adjustment disorder with predominant disturbance of conduct, adjustment disorder with mixed disturbance of emotions and conduct and adjustment disorders with other specified predominant symptoms; and other reactions to severe stress.

In particular, the compounds according to the invention are useful in the treatment or prevention of sleep disorders, including but not limited to dysomnia and/or parasomnias as primary sleep disorders; insomnia; sleep apnea; narcolepsy; circadian rhythms disorders; sleep disorders related to another mental disorder; sleep disorder due to a general medical condition; and substance-induced sleep disorder.

In particular, the compounds according to the invention are useful in the treatment or prevention of cognitive disorders, including but not limited to dementia; amnesic disorders and cognitive disorders not otherwise specified, especially dementia caused by degenerative disorders, lesions, trauma, infections, vascular disorders, toxins, anoxia, vitamin deficiency or endocrinic disorders; dementia of the Alzheimer's type, with early or late onset, with depressed mood; AIDS-associated dementia or amnesic disorders caused by alcohol or other causes of thiamin deficiency, bilateral temporal lobe damage due to Herpes simplex encephalitis and other limbic encephalitis, neuronal loss secondary to anoxia/hypoglycemia/severe convulsions and surgery, degenerative disorders, vascular disorders or pathology around ventricle III. Furthermore, the compounds according to the invention are also useful as memory and/or cognition enhancers in healthy humans with no cognitive and/or memory deficit.

In particular, the compounds according to the invention are useful in the treatment or prevention of personality disorders, including but not limited to paranoid personality disorder; schizoid personality disorder; schizotypical personality disorder; antisocial personality disorder; borderline personality disorder; histrionic personality disorder; narcissistic personality disorder; avoidant personality disorder; dependent personality disorder; obsessive-compulsive personality disorder and personality disorder not otherwise specified.

In particular, the compounds according to the invention are useful in the treatment or prevention of schizoaffective disorders resulting from various causes, including schizoaffective disorders of the manic type, of the depressive type, of mixed type; paranoid, disorganized, catatonic, undifferentiated and residual schizophrenia; schizophreniform disorder; schizoaffective disorder; delusional disorder; brief psychotic disorder; shared psychotic disorder; substance-induced psychotic disorder and psychotic disorder not otherwise specified.

In particular, the compounds according to the invention are also useful in the treatment or prevention of eating disorders, including anorexia nervosa; atypical anorexia nervosa; bulimia nervosa; atypical bulimia nervosa; overeating associated with other psychological disturbances; vomiting associated with other psychological disturbances; and non-specified eating disorders.

In particular, the compounds according to the invention are also useful in the treatment or prevention of neurodegenerative diseases, including but not limited to Alzheimer's disease; Huntington's chorea; Creutzfeld-Jacob disease; Pick's disease; demyelinating disorders, such as multiple sclerosis and ALS; other neuropathies and neuralgia; multiple sclerosis; amyotropical lateral sclerosis; stroke and head trauma.

In particular, the compounds according to the invention are also useful in the treatment or prevention of addiction disorders, including but not limited to substance dependence or abuse with or without physiological dependence, particularly where the substance is alcohol, amphetamines, amphetamine-like substances, caffeine, cocaine, hallucinogens, inhalants, nicotine, opioids (such as cannabis, heroin and morphine), phencyclidine, phencyclidine-like compounds, sedative-hypnotics, benzodiazepines and/or other substances, particularly useful for treating withdrawal from the above substances and alcohol withdrawal delirium.

In particular, the compounds according to the invention are also useful in the treatment or prevention of mood disorders induced particularly by alcohol, amphetamines, caffeine, cannabis, cocaine, hallucinogens, inhalants, nicotine, opioids, phencyclidine, sedatives, hypnotics, anxiolytics and other substances.

In particular, the compounds according to the invention are also useful in the treatment or prevention of sexual dysfunction, including but not limited to sexual desire disorders; sexual arousal disorders; orgasmic disorders; sexual pain disorders; sexual dysfunction due to a general medical condition; substance-induced sexual dysfunction and sexual dysfunction not otherwise specified.

In particular, the compounds according to the invention are also useful in the treatment or prevention of pain, including but not limited to traumatic pain such as postoperative pain; traumatic avulsion pain such as brachial plexus; chronic pain such pancreatitis induced chronic pain or arthritic pain such as occurring in osteo-rheumatoid or psoriatic arthritis; neuropathic pain such as post-herpetic neuralgia, trigeminal neuralgia, segmental or intercostal neuralgia, fibromyalgia, causalgia, peripheral neuropathy, diabetic neuropathy, chemotherapy-induced neuropathy, AIDS related neuropathy, occipital neuralgia, geniculate neuralgia, glossopharyngeal neuralgia, reflex sympathetic dystrophy and phantom limb pain; various forms of headache such as migraine, acute or chronic tension headache, temporomandibular pain, maxillary sinus pain and cluster headache; odontalgia; cancer pain; visceral pain gastrointestinal pain; nerve entrapment pain; sport's injury pain; dysmennorrhoea; menstrual pain; meningitis; arachnoiditis; musculoskeletal pain; low back pain such as spinal stenosis, prolapsed disc, sciatica, angina, ankylosing spondyolitis; gout; burns; scar pain; itch; and thalamic pain such as post stroke thalamic pain.

In particular, the compounds according to the invention are also useful in the treatment or prevention of the following other CNS-related conditions: akinesia, akinetic-rigid syndromes, dyskinesia and medication-induced parkinsonism, Gilles de la Tourette syndrome and its symptoms, tremor, chorea, myoclonus, tics and dystonia, attention-deficit/hyperactivity disorder (ADHD), Parkinson's disease, drug-induced Parkinsonism, post-encephalitic Parkinsonism, progressive supranuclear palsy, multiple system atrophy, corticobasal degeneration, parkinsonism-ALS dementia complex and basal ganglia calcification, behavioral disturbances and conduct disorders in dementia and the mentally retarded, including restlessness and agitation, extra-pyramidal movement disorders, Down's syndrome and Akathisia.

In particular, the compounds according to the invention are also useful in the treatment or prevention of inflammation, including but not limited to inflammatory conditions in asthma, influenza, chronic bronchitis and rheumatoid arthritis; inflammatory conditions in the gastrointestinal tract such as, but not limited to Crohn's disease, ulcerative colitis, inflammatory bowel disease and non-steroidal anti-inflammatory drug induced damage; inflammatory conditions of the skin such as herpes and eczema; inflammatory conditions of the bladder such as cystitis and urge incontinence; and eye and dental inflammation and pancreatitis, in particular chronic and acute pancreatitis.

In particular, the compounds according to the invention are also useful in the treatment or prevention of allergic disorders, including but not limited to allergic disorders of the skin such as but not limited to urticaria; and allergic disorders of the airways such as but not limited to rhinitis.

In particular, the compounds according to the invention are also useful in the treatment or prevention of emesis, i.e. nausea, retching and vomiting, including but not limited to acute emesis, delayed emesis and anticipatory emesis; emesis induced by drugs such as cancer chemotherapeutic agents such as alkylating agents, for example cyclophosphamide, carmustine, lomustine and chlorambucil; cytotoxic antibiotics, for example dactinomycin, doxorubicin, mitomycin-C and bleomycin; anti-metabolites, for example cytarabine, methotrexate and 5-fluorouracil; vinca alkaloids, for example etoposide, vinblastine and vincristine; and other drugs such as cisplatin, dacarbazine, procarbazine and hydroxyurea; and combinations thereof; radiation sickness; radiation therapy, such as in the treatment of cancer; poisons; toxins such as toxins caused by metabolic disorders or by infection, such as gastritis, or released during bacterial or viral gastrointestinal infection; pregnancy; vestibular disorders, such as motion sickness, vertigo, dizziness and Meniere's disease; post-operative sickness; gastrointestinal obstruction; reduced gastrointestinal motility; visceral pain, such as myocardial infarction or peritonitis; migraine; increased intracranial pressure; decreased intracranial pressure (such as altitude sickness); opioid analgesics, such as morphine; gastro-oesophageal reflux disease; acid indigestion; over-indulgence of food or drink; acid stomach; sour stomach; waterbrash/regurgitation; heartburn, such as episodic heartburn, nocturnal heartburn and meal induced heartburn; and dyspepsia.

In particular, the compounds according to the invention are also useful in the treatment or prevention of gastrointestinal disorders, including but not limited to irritable bowel syndrome (IBS), skin disorders such as psoriasis, pruritis and sunburn; vasospastic diseases such as angina, vascular headache and Reynaud's disease, cerebral ischaemia such as cerebral vasospasm following subarachnoid haemorrhage; fibrosing and collagen diseases such as scleroderma and eosinophilic fascioliasis; disorders related to immune enhancement or suppression such as systemic lupus erythematosus and rheumatic diseases such as fibrositis; cough; and body weight control, including obesity.

The present invention also relates to a method for the treatment and/or prophylaxis of neurokinin-mediated diseases, in particular for the treatment and/or prophylaxis of depression, anxiety disorders, emesis and irritable bowel syndrome (IBS) comprising administering to a human in need of such administration an effective amount of a compound according to the invention, in particular according to Formula (I), the pharmaceutically acceptable acid or base addition salts thereof, the stereochemically isomeric forms thereof, the N-oxide form thereof, as well as the pro-drugs thereof.

The invention also relates to a pharmaceutical composition comprising a pharmaceutically acceptable carrier and, as active ingredient, a therapeutically effective amount of a compound according to the invention, in particular a compound according to Formula (I), the pharmaceutically acceptable acid or base addition salts thereof, the stereochemically isomeric forms thereof, the N-oxide form thereof and a pro-drug thereof.

The compounds according to the invention, in particular the compounds according to Formula (I), the pharmaceutically acceptable acid or base addition salts thereof, the stereochemically isomeric forms thereof, the N-oxide form thereof and the prodrugs thereof, or any subgroup or combination thereof may be formulated into various pharmaceutical forms for administration purposes. As appropriate compositions there may be cited all compositions usually employed for systemically administering drugs. To prepare the pharmaceutical compositions of this invention, an effective amount of the particular compound, optionally in addition salt form, as the active ingredient is combined in intimate admixture with a pharmaceutically acceptable carrier, which carrier may take a wide variety of forms depending on the form of preparation desired for administration. These pharmaceutical compositions are desirable in unitary dosage form suitable, in particular, for administration orally, rectally, percutaneously, by parenteral injection or by inhalation. For example, in preparing the compositions in oral dosage form, any of the usual pharmaceutical media may be employed such as, for example, water, glycols, oils, alcohols and the like in the case of oral liquid preparations such as suspensions, syrups, elixirs, emulsions and solutions; or solid carriers such as starches, sugars, kaolin, diluents, lubricants, binders, disintegrating agents and the like in the case of powders, pills, capsules and tablets. Because of their ease in administration, tablets and capsules represent the most advantageous oral dosage unit forms in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. Also included are solid form preparations that are intended to be converted, shortly before use, to liquid form preparations. In the compositions suitable for percutaneous administration, the carrier optionally comprises a penetration enhancing agent and/or a suitable wetting agent, optionally combined with suitable additives of any nature in minor proportions, which additives do not introduce a significant deleterious effect on the skin. Said additives may facilitate the administration to the skin and/or may be helpful for preparing the desired compositions. These compositions may be administered in various ways, e.g., as a transdermal patch, as a spot-on, as an ointment.

It is especially advantageous to formulate the aforementioned pharmaceutical compositions in unit dosage form for ease of administration and uniformity of dosage. Unit dosage form as used herein refers to physically discrete units suitable as unitary dosages, each unit containing a predetermined quantity of active ingredient calculated to produce the desired therapeutic effect in association with the required pharmaceutical carrier. Examples of such unit dosage forms are tablets (including scored or coated tablets), capsules, pills, powder packets, wafers, suppositories, injectable solutions or suspensions and the like, and segregated multiples thereof.

Since the compounds according to the invention are potent orally administrable $NK_1$ antagonists, pharmaceutical compositions comprising said compounds for administration orally are especially advantageous.

Preparation

The compounds according to the invention can generally be prepared by a succession of steps, each of which is known to the skilled person.

The compounds of Formula (I) are conveniently prepared by reductively N-alkylating an intermediate of Formula (II) wherein $R^1$, $R^2$, X, Q, m, n and p are defined as in Formula (I), with a N-substituted piperidinon of Formula (III) wherein $R^1$, Alk, Y, L and q are defined as in Formula (I). Said reductive N-alkylation may be performed in a reaction-inert solvent such as, for example, dichloromethane, ethanol or toluene or a mixture thereof, and in the presence of an appropriate reducing agent such as, for example, a borohydride, e.g. sodium borohydride, sodium cyanoborohydride or triacetoxy borohydride. In case a borohydride is used as a reducing agent, it may be convenient to use a complex-forming agent such as, for example, titanium(IV)-isopropylate as described in J. Org. Chem, 1990, 55, 2552-2554. Using said complex-forming agent may also result in an improved cis/trans ratio in favor of the trans isomer. It may also be convenient to use hydrogen as a reducing agent in combination with a suitable catalyst such as, for example, palladium-on-charcoal or platinum-on-charcoal. In case hydrogen is used as reducing agent, it may be advantageous to add a dehydrating agent to the reaction mixture such as, for example, aluminium tert-butoxide. In order to prevent the undesired further hydrogenation of certain functional groups in the reactants and the reaction products, it may also be advantageous to add an appropriate catalyst-poison to the reaction mixture, e.g., thiophene or quinoline-sulphur. Stirring and optionally elevated temperatures and/or pressure may enhance the rate of the reaction.

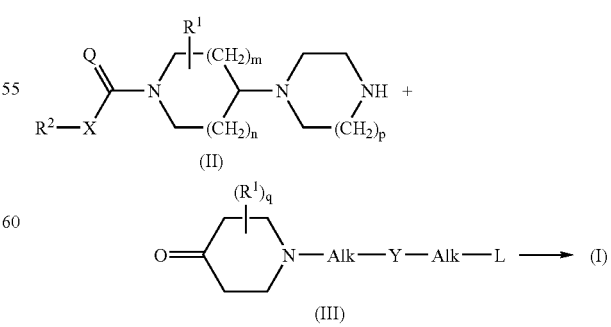

In this and the following preparations, the reaction products may be isolated from the reaction medium and, if necessary, further purified according to methodologies generally known in the art such as, for example, extraction, crystallization, trituration and chromatography.

Especially advantage is the preparation of a compound according to the invention according to the previous reaction scheme in which the Alk-Y-Alk-L-moiety is benzyl, thus giving rise to a compound according to Formula (I) in which the Alk-Y-Alk-L-moiety is benzyl. Said compound is pharmacological active and can be converted into a compound according to the invention in which the Alk-Y-Alk-L-moiety is hydrogen by reductive hydrogenation using e.g. hydrogen as a reducing agent in combination with a suitable catalyst such as, for example, palladium-on-charcoal or platinum-on-charcoal. The resulting compound according to the invention can then be converted into other compounds according to the invention by art-known transformations, e.g. acylation and alkylation.

In particular, the compounds of Formula ($I^a$) can be prepared by reacting a final compound of Formula (I') wherein $R^1$, $R^2$, X, Q, m, n, p and q are defined as in Formula (I) with an acyl compound of Formula (V) wherein Alk and L are defined as in Formula (I) and $W^1$ is an appropriate leaving group such as, for example, a halo, e.g. chloro or bromo, or a sulfonyloxy leaving group, e.g. methanesulfonyloxy or benzenesulfonyloxy. The reaction can be performed in a reaction-inert solvent such as, for example, a chlorinated hydrocarbon, e.g. dichloromethane, an alcohol, e.g. ethanol, or a ketone, e.g. methyl isobutylketone, and in the presence of a suitable base such as, for example, sodium carbonate, sodium hydrogen carbonate or triethylamine. Stirring may enhance the rate of the reaction. The reaction may conveniently be carried out at a temperature ranging between room temperature and reflux temperature.

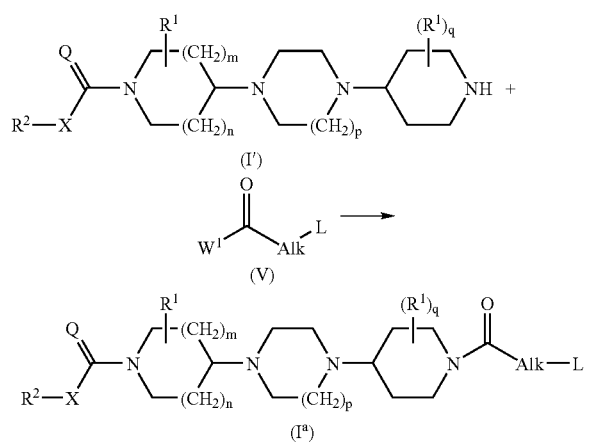

Alternatively, the compounds of Formula ($I^a$) can also be prepared by reacting a final compound of Formula (I') wherein $R^1$, $R^2$, X, Q, m, n, p and q are defined as in Formula (I) with a carboxylic acid of Formula (VI) wherein Alk and L are defined as in Formula (I)(base-catalyzed nucleophilic addition reaction). The reaction can be performed in a reaction-inert solvent such as, for example, a chlorinated hydrocarbon, e.g. dichloromethane, an alcohol, e.g. ethanol, or a ketone, e.g. methyl isobutylketone, and in the presence of a suitable base such as, for example, sodium carbonate, sodium hydrogen carbonate or triethylamine. Stirring may enhance the rate of the reaction. The reaction may conveniently be carried at a temperature ranging between room temperature and reflux temperature.

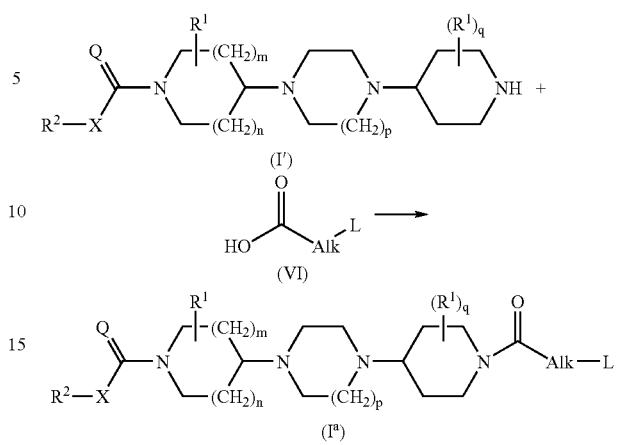

The above reaction may also be carried out under equivalent conditions with the carboxylic ester of the carboxylic acid of Formula (VI).

In particular, the compounds of Formula ($I^b$) can be prepared by reacting a final compound of Formula (I') wherein $R^1$, $R^2$, X, Q, m, n, p and q are defined as in Formula (I) with a keto-compound of Formula (VII) wherein $W^2$ is an appropriate leaving group such as, for example, a halogen, e.g. chloro or bromo, or a sulfonyloxy leaving group, e.g. methanesulfonyloxy or benzenesulfonyloxy. The reaction can be performed in a reaction-inert solvent such as, for example, a chlorinated hydrocarbon, e.g. dichloromethane, an alcohol, e.g. ethanol, or a ketone, e.g. methyl isobutylketone, and in the presence of a suitable base such as, for example, sodium carbonate, sodium hydrogen carbonate or triethylamine. Stirring may enhance the rate of the reaction. The reaction may conveniently be carried at a temperature ranging between room temperature and reflux temperature.

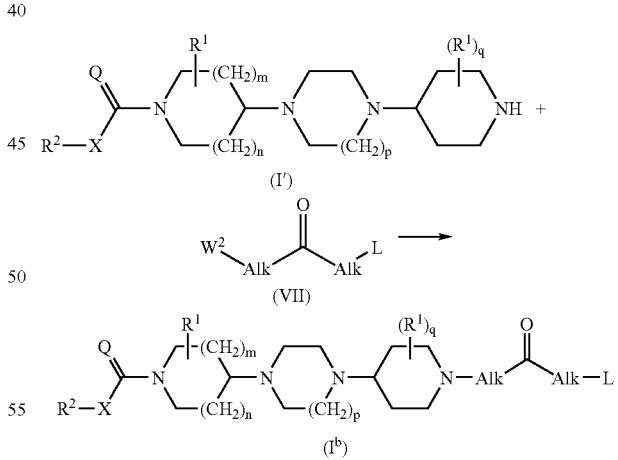

The compounds of Formula ($I^c$) can be prepared by reductive amination/alkylation of a final compound of Formula (I') wherein $R^1$, $R^2$, X, Q, m, n, p and q are defined as in Formula (I) with a compound of Formula (VIII) wherein Alk and L are defined as in Formula (I) and $W^3$ is an appropriate leaving group such as, for example, a halogen, e.g. chloro or bromo, or a sulfonyloxy leaving group, e.g. methanesulfonyloxy or benzenesulfonyloxy. The reaction can be performed in a reaction-inert solvent such as, for example, a chlorinated hydrocarbon, e.g. dichloromethane, an alcohol, e.g. ethanol, or a ketone, e.g. methyl isobutylketone, and in the presence of a suitable base such as, for example, sodium carbonate, sodium hydrogen carbonate or triethylamine. Stirring may enhance the rate of the reaction. The reaction may conveniently be carried at a temperature ranging between room temperature and reflux temperature.

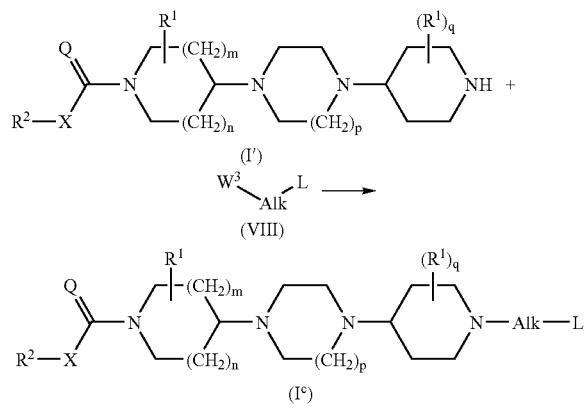

The starting materials and some of the intermediates are known compounds and are commercially available or may be prepared according to conventional reaction procedures generally known in the art. For example, intermediates of formula (II) may be prepared by reductively N-alkylating an intermediate of formula (IX) with an intermediate of formula (X) in which $W^4$ is a benzyl radical, after which the compound according to Formula (X) is subsequently reduced to yield an intermediate compound according to Formula (II). Said reductive N-alkylation may be performed in a reaction-inert solvent such as, for example, dichloromethane, ethanol, toluene or a mixture thereof, and in the presence of an appropriate reducing agent such as, for example, a borohydride, e.g. sodium borohydride, sodium cyanoborohydride or triacetoxy borohydride. In case a borohydride is used as a reducing agent, it may be convenient to use a complex-forming agent such as, for example, titanium(IV)isopropylate as described in J. Org. Chem, 1990, 55, 2552-2554. Using said complex-forming agent may also result in an improved cis/trans ratio in favor of the trans isomer. It may also be convenient to use hydrogen as a reducing agent in combination with a suitable catalyst such as, for example, palladium-on-charcoal or platinum-on-charcoal. In case hydrogen is used as reducing agent, it may be advantageous to add a dehydrating agent to the reaction mixture such as, for example, aluminium tert-butoxide. In order to prevent the undesired further hydrogenation of certain functional groups in the reactants and the reaction products, it may also be advantageous to add an appropriate catalyst-poison to the reaction mixture, e.g., thiophene or quinoline-sulphur. Stirring and optionally elevated temperatures and/or pressure may enhance the rate of the reaction.

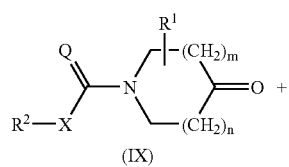

-continued

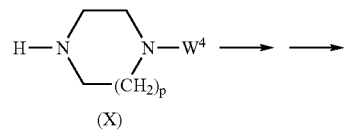

The preparation of these and other intermediates is described in WO 97/16440-A1, published May 9, 1997 by Janssen Pharmaceutica N.V, which is disclosed herein by reference as well as in other publications mentioned in WO 97/16440-A1, such as, e.g. EP-0,532,456-A.

Compounds according to the invention may be converted into each other following art-known transformation reactions, such as illustrated further.

More specifically, compounds of Formula (XIII), wherein A is an aryl or heteroaryl, Z may be any moiety, preferably a moiety $Z^1$ as defined below, Het is an unsaturated heteroaryl and r is an integer ranging from 1 to a number equal to the number of available carbon atoms in the aryl or heteroaryl-moiety A, e.g. 5 in phenyl and 4 in pyrrolyl, may be obtained by a novel type of Heck-reaction wherein a compound of Formula (XI), wherein Z, A and r are as defined in Formula (XIII) and Hal is a halogen, thus comprising an active or non-active halo-substituted aryl or halo-substituted heteroaryl, more preferably a mono or polysubstituted bromo- and/or iodoaryl or -heteroaryl moiety is reacted with an unsaturated heteroaryl according to Formula (XII) in the presence of catalytic amounts of $Pd(OAc)_2$ and 1,3-bis diphenylphosphinopropane, in the presence of a suitable base, preferably $Cs_2CO_3$ or K(AcO), in a reaction-inert polar solvent such as, preferably NMP, DMA, DMF or the like and at an elevated reaction temperature, preferably at 140-150° C. for a certain period of time, preferably about 6-20 hours, more preferably 12-18 hours.

Preferably, r is 1. Het may be a unsaturated monocyclic or bicyclic heteroaryl moiety, such as for instance imidazo[1,2-α]pyridinyl, pyrrolyl, thienyl, thiazolyl, imidazolyl, oxazolyl, furanyl, thienyl, benzimidazolyl, benzoxazolyl, benzthiazolyl, benzofuranyl, benzothienyl or indolyl or such as any of the unsaturated radicals in the groups $Het^1$ and $Het^2$ as defined in Formula (I), optionally substituted with one or more radicals selected from the group of $Ar^1$, $Ar^1$alkyl, halo, hydroxy, alkyl, piperidinyl, pyrrolyl, thienyl, oxo, alkyloxy, alkyloxyalkyl and alkyloxycarbonyl. Preferably, A is phenyl or pyridinyl.

Said reaction has an improved yield over the process according to the prior art (Yutaka Aoyagi et al., *Heterocycles*, 1992, 33, 257 and Sommai Pivsa-Art, *Bull. Chem. Soc. Jpn.*, 1998, 71, 467).

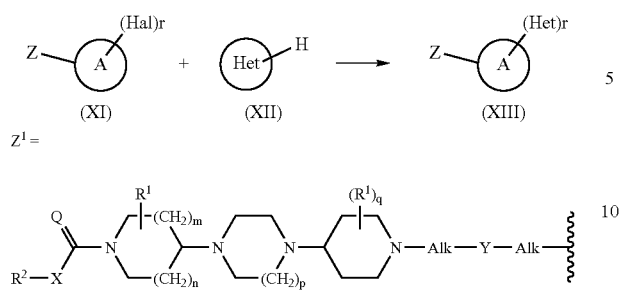

$Z^1 =$

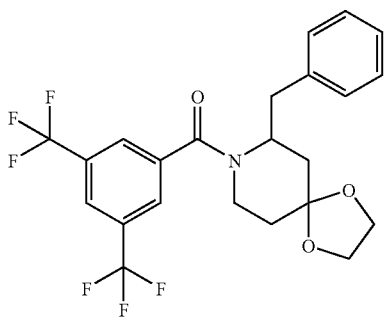

Also, compounds according to the invention may be converted into an acid addition salt by treatment with an acid, or into a base addition salt by treatment with a base, or conversely, the acid addition salt form may be converted into the free base by treatment with alkali, or the base addition salt may be converted into the free acid by treatment with an acid.

The following examples are intended to illustrate and not to limit the scope of the present invention.

Experimental Part

Hereinafter "RT" means room temperature, "CDI" means 1,1'-carbonyldiimidazole, "DIPE" means diisopropylether, "MIK" means methyl isobutyl keton, "BINAP" means [1,1'-binaphthalene]-2,2'-diylbis[diphenylphosphine], "NMP" means 1-methyl-2-pyrrolidinone, "$Pd_2(dba)_3$" means tris(dibenzylideneacetone)dipalladium and "DMF" means N,N-dimethylformamide.

PREPARATION OF THE INTERMEDIATE COMPOUNDS

Example A1 a. Preparation of Intermediate Compound 1

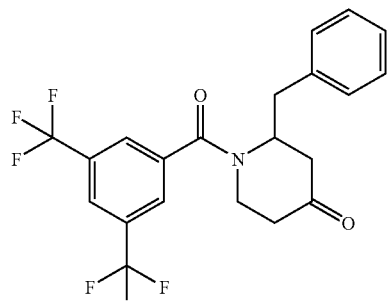

$Et_3N$ (0.55 mol) was added to a stirring mixture of 7-(phenylmethyl)-1,4-dioxa-8-azaspiro[4.5]decane (0.5 mol) in toluene (1500 ml). 3,5-Bis(trifluoromethyl)benzoyl chloride (0.5 mol) was added over a 1-hour period (exothermic reaction). The mixture was stirred at room temperature for 2 hours, then allowed to stand for the weekend and washed three times with water (500 ml, 2×250 ml). The organic layer was separated, dried, filtered and the solvent was evaporated. Yielding: 245 g (100%). Part of this fraction was crystallized from petroleum ether. The precipitate was filtered off and dried. Yielding: 1.06 g of intermediate compound 1.

b. Preparation of Intermediate Compound 2

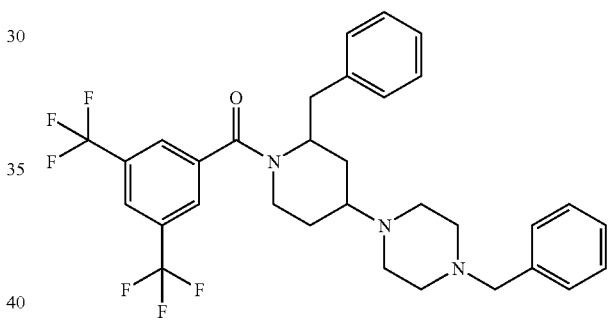

HCl cp (300 ml) was added to a mixture of intermediate compound 1 (0.5 mol) in ethanol (300 ml) and $H_2O$ (300 ml). The reaction mixture was stirred at 60° C. for 20 hours. The precipitate was filtered off, ground, stirred in $H_2O$, filtered off, washed with petroleum ether and dried. Yielding: 192 g of intermediate compound 2 ((+−)-1-[3,5-bis(trifluoromethyl)benzoyl]-2-(phenylmethyl)-4-piperidinone) (89.4%) (mixture of R and S enantiomers).

c. Preparation of Intermediate Compound 3

A mixture of intermediate compound 2 (0.046 mol), 1-(phenylmethyl)piperazine (0.051 mol) and C (0.056 mol) was stirred for 2 hours at 40° C. The reaction mixture was cooled to room temperature. Ethanol, p.a. (350 ml) was added. $BH_4Na$ (0.138 mol) was added. The resulting reaction mixture was stirred for one hour at room temperature, then for one hour at 50° C. More $BH_4Na$ (5.2 g) was added and the reaction mixture was stirred for 2 hours at 50° C. Again, $BH_4Na$ was added and the reaction mixture was stirred overnight at room temperature, then for 2 hours at 50° C. Water (10 ml) was added. The mixture was stirred for 15 min. $CH_2Cl_2$ (200 ml) was added and the mixture was stirred for 15 min. The organic phase was separated, dried ($MgSO_4$), dicalite was added, the mixture was filtered over dicalite, and the filtrate was evaporated. This fraction was separated into (CIS) and (TRANS) by column chromatography over silica gel. The desired (TRANS)-fractions were collected and the solvent was evaporated, giving 14.8 g of residue ((I), 1.06% (CIS)) and 4.9 g of residue ((II), 6% (CIS)). Resolution and purification of those (TRANS)-fractions (±20 g in total) was obtained by chromatography over stationary phase Chiralcel OD (1900 Gr) in Prochrom LC110 35 bar (eluent: hexane/ethanol 90/10). The desired fractions were collected and the solvent was evaporated. Yielding: 9.5 g of intermediate compound 3 (2R-trans)-1-[3,5-bis(trifluoromethyl)benzoyl]-2-(phenylmethyl)-4-[4-(phenylmethyl)-1-piperazinyl]piperidine.

d. Preparation of Intermediate Compound 4

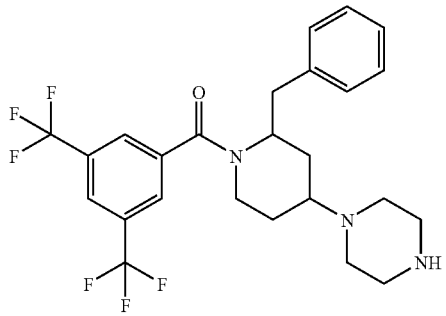

A mixture of intermediate compound 3 (0.288 mol) in methanol (700 ml) was hydrogenated at 40° C. with Pd/C, 10% (5 g) as a catalyst. After uptake of H$_2$ (1 equiv), the catalyst was filtered off and the filtrate was evaporated. Yielding: 141.2 g of intermediate compound 4 (+)-(2R-trans)-1-[3,5-bis(trifluoromethyl)benzoyl]-2-(phenylmethyl)-4-(1-piperazinyl)piperidine.

Example A2

Preparation of Intermediate Compound 5

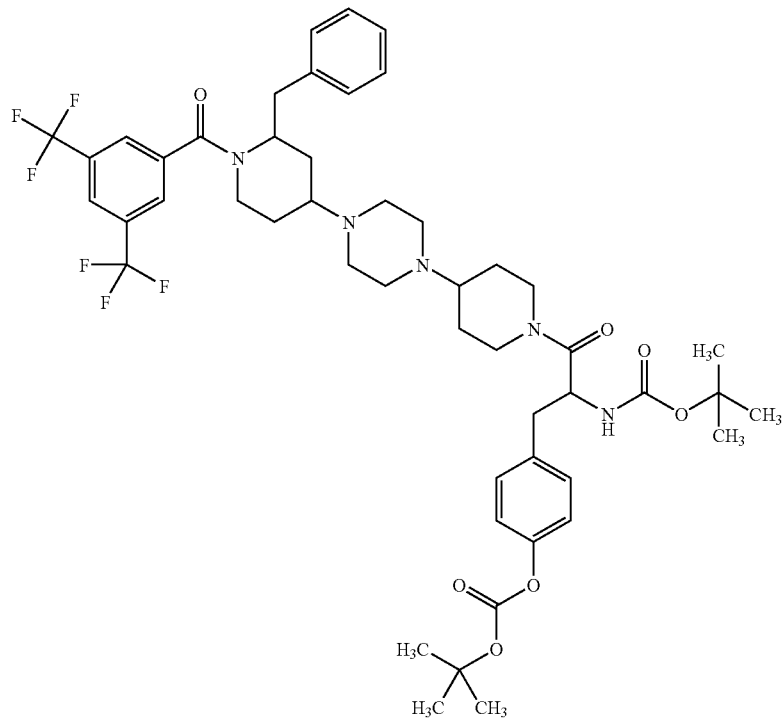

A mixture of N-[(1,1-dimethylethoxy)carbonyl]-L-tyrosine 1,1-dimethylethylcarbonate (0.005 mol), N,N-dimethyl-4-pyridinamine (0.006 mol) and Et$_3$N (0.006 mol) in CH$_2$Cl$_2$, p.a. (10 ml) was stirred at room temperature. N-(ethylcarbonimidoyl)-N,N-dimethyl-1,3-propanediamine monohydrochloride (0.006 mol) was added portionwise and was stirred for 45 minutes at room temperature. Then final compound 2 (described in example B1.b) (0.005 mol) was added and the reaction mixture was stirred overnight at room temperature. The mixture was washed with H$_2$O and Na$_2$CO$_3$. The separated organic layer was dried, filtered and the solvent was evaporated. The residue was purified over silicagel on a glass filter (eluent: CH$_2$Cl$_2$/MeOH 100/0;98/2;96/4;94/6). The purest fractions were collected and the solvent was evaporated. Yield: 1.4 g intermediate compound 5 (30%).

Example A3 a. Preparation of Intermediate Compound 6

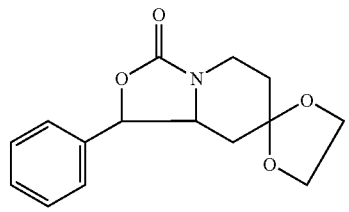

A mixture of 7-(hydroxyphenylmethyl)-1,4-dioxa-8-azaspiro[4,5]decane-8-carboxylic acid 1,1-dimethylethyl ester (0.5 mol) and 2-methyl-2-propanol potassium salt (6 g) in toluene (900 ml) was stirred and refluxed for 2 h. The mixture was evaporated and the residue was stirred up in petrol ether and a little water. The mixture was decanted and the residue was stirred up in DIPE. The precipitate was filtered off and dried. Yielding: 127.4 g of intermediate compound 6 (92%).

b. Preparation of Intermediate Compound 7

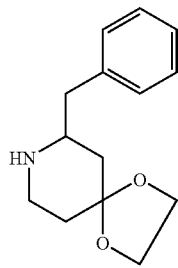

A mixture of intermediate compound 6 (0.5 mol) in methanol (700 ml) was hydrogenated at 50° C. overnight with Pd/C, 10% (5 g) as a catalyst. After uptake of $H_2$ (1 eq), the catalyst was filtered off and the filtrate was evaporated. The residue was taken up in water and extracted with $CH_2Cl_2$. The organic layer was dried ($MgSO_4$), filtered off and evaporated. Yielding: 99 g intermediate compound 7 (85%).

c. Preparation of Intermediate Compound 8

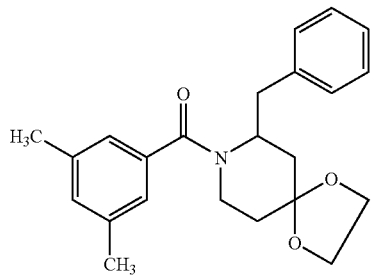

$Et_3N$ (0.55 mol) was added to a mixture of intermediate compound 7 (0.5 mol) in toluene (1500 ml). 3,5-Dimethylbenzoyl chloride (0.5 mol) was added dropwise slowly over a 1-hour period while the temperature was kept below 50° C. and while stirring was continued. The mixture was stirred at room temperature overnight, then washed three times with water (500 ml, 2×250 ml) and separated into its layers. The organic layer was dried ($MgSO_4$), filtered and the solvent was evaporated. Yielding: 197 g (113%). Part of this fraction was dried. Yielding: 0.65 g of intermediate compound 8.

d. Preparation of Intermediate Compound 9

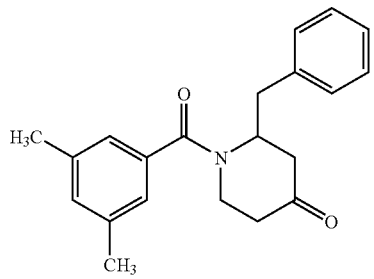

A mixture of intermediate compound 8 (0.56 mol) in ethanol (300 ml), HCl (300 ml) and $H_2O$ (300 ml) was stirred at 60° C. for 8 hours. The mixture was stirred at room temperature for the weekend. The precipitate was filtered off, taken up in water, filtered off, washed with petroleum ether and dried. Yielding: 140.9 g of intermediate compound 9 (88%).

e. Preparation of Intermediate Compound 10

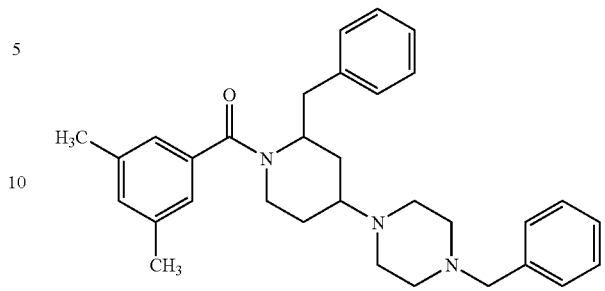

A mixture of intermediate compound 9 (0.05 mol) and 1-(phenylmethyl)-piperazine (0.05 mol) in thiophene, 4% solution (2 ml) and toluene (500 ml) was hydrogenated with Pd/C, 10% (1 g) as a catalyst. After uptake of $H_2$ (1 eq), the catalyst was filtered off and the filtrate was evaporated. The residue was purified by column chromatography over silica gel (eluent: $CH_2Cl_2/(CH_3OH/NH_3)$ 99/1). The pure fractions were collected and evaporated. Yielding: 17.07 g (71%). The pure fractions of fraction 1 were collected and evaporated. Yielding: 2.5 g of intermediate compound. 10 (10%).

f. Preparation of Intermediate Compound 11

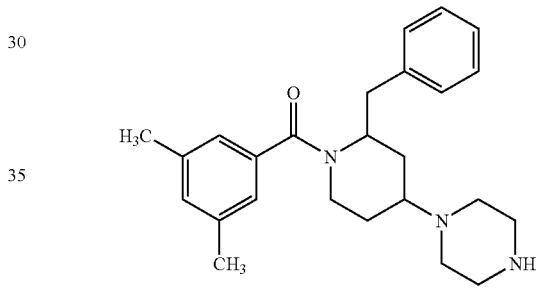

A mixture of intermediate compound 10 (0.0052 mol) in methanol (100 ml) was hydrogenated at 50° C. for one night with Pd/C, 10% (1 g) as a catalyst. After uptake of $H_2$ (1 eq), the catalyst was filtered off and the filtrate was evaporated. The residue was purified on a glass filter over silica gel (eluent: $CH_2Cl_2/(CH_3OH/NH_3)$ 99/1, 98/2, 97/3, 96/4 and 95/5). The pure fractions were collected and evaporated. Yielding: 1.7 g on intermediate compound 11 (83%).

Example A4

Preparation of Intermediate Compound 12

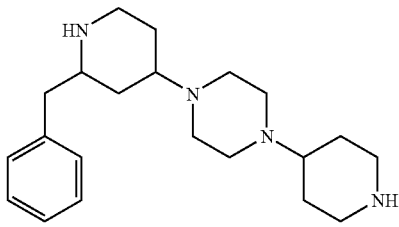

A mixture of final compound 2 (prepared according to B1b) (0.01 mol) and KOH (0.15 mol) in 2-propanol (50 ml) was stirred and refluxed for 18 hours. The solvent was evaporated, then the residue was taken up in H₂O (20 ml) and the mixture was extracted with CH₂Cl₂. The organic layer was washed with NaOH (1N), dried (MgSO₄), filtered and the solvent was evaporated. Yield: 3.25 g of intermediate compound 12 (95%).

Preparation of the Final Compounds

Example B1 a. Preparation of Final Compound 1

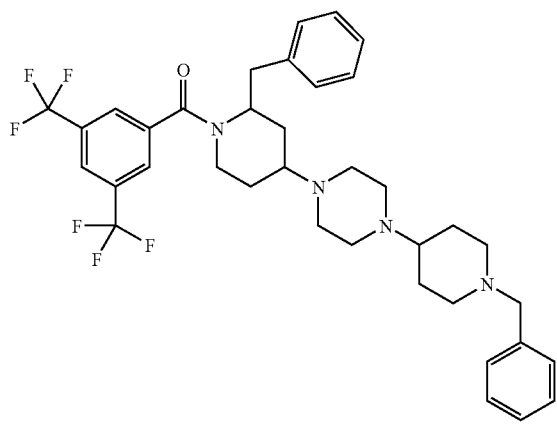

A mixture of intermediate compound 4 (0.12 mol) and 1-(phenylmethyl)-4-piperidinone (0.12 mol) in methanol (250 ml) was hydrogenated at 50° C. with Pd/C 10% (3 g) as a catalyst in the presence of thiophene solution (2 ml). After uptake of H₂ (1 equiv), the catalyst was filtered off and the filtrate was evaporated. The residue was suspended in petroleum ether, filtered off and crystallized from DIPE. Yield: 46 g (F1). The filtrate was evaporated. Yield: 37.7 g (F2). F1 and F2 were combined and purified by column chromatography over silica gel (eluent: CH₂Cl₂/MeOH 91/9). The product fractions were collected and the solvent was evaporated. Yield: 46 g (F3). Part of F3 was crystallized from DIPE. Yield: 0.65 g of final compound 1.

b. Preparation of Final Compound 2

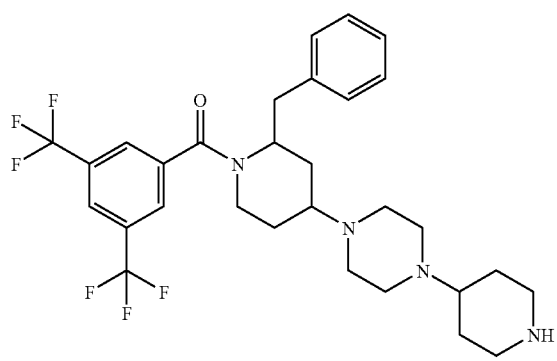

A mixture of final compound 1 (0.0074 mol) in methanol (150 ml) was hydrogenated with Pd/C 10% (1 g) as a catalyst. After uptake of H₂ (1 equiv), the catalyst was filtered off and the filtrate was concentrated. Yield: 4.3 g of final compound 2.

Example B2

Preparation of Final Compound 3

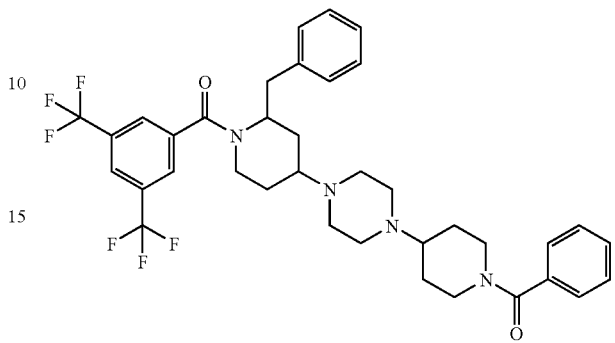

A mixture of final compound 2 (0.0015 mol) and Et₃N (0.1 mol) in CH₂Cl₂ (100 ml) was stirred at room temperature. Benzoylchloride (0.0025 mol) was dissolved in CH₂Cl₂ and added dropwise to the reaction mixture. The mixture was stirred for 1 hour at room temperature. NaOH (1N; 100 ml) was added and the mixture was stirred for 30 minutes at room temperature. The separated aqueous layer was extracted with CH₂Cl₂. The organic layer was washed with H₂O, dried (MgSO₄), filtered and the solvent was evaporated. The residue was purified by column chromatography over silica gel (eluent: CH₂Cl₂/MeOH 100/0;90/10). The desired fractions were collected and the solvent was evaporated. Yield: 0.624 g of final compound 3. (61%).

Example B3 a. Preparation of Final Compound 4

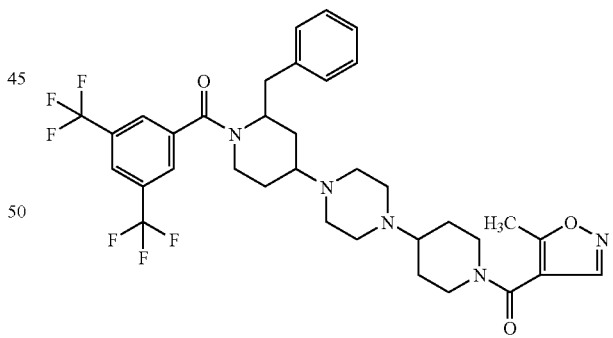

A mixture of 5-methyl-4-isoxazolecarboxylic acid (0.0015 mol) in CH₂Cl₂ (20 ml) and 1,1'-carbonylbis-1H-imidazole (0.0015 mol) was stirred for 2 hours at room temperature. Final compound 2 (prepared according to B1.b) (0.001 mol) was added. After stirring overnight, the reaction mixture was washed with diluted NaOH, washed with H₂O, dried, filtered and the solvent evaporated. The residue was purified by column chromatography over silica gel (eluent: CH₂Cl₂-gradient 0->10% MeOH). The product fractions were collected and the solvent evaporated. The residue was dried. Yield: 0.204 g of final compound 4.

b. Preparation of Final Compound 5

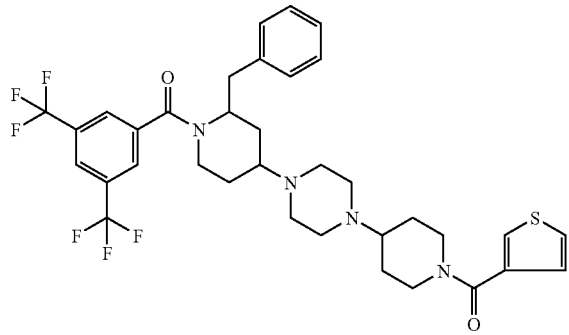

A mixture of 3-thiophenecarboxylic acid (0.00188 mol), N,N-dimethyl-4-pyridinamine (0.00255 mol) and Et$_3$N (0.00255 mol) in CH$_2$Cl$_2$ (200 ml) was stirred at room temperature. N,N-dimethyl-N'-(methylcarbonimidoyl)-1,3-propanediamine (0.00255 mol) was added portionwise and the mixture was stirred for one hour at room temperature. A solution of final compound 2 (prepared according to B1b) (0.00188 mol) in CH$_2$Cl$_2$ was added dropwise and the reaction mixture was stirred over the weekend at room temperature. The mixture was poured out into 1 g NaOH/water. The layers were separated. The water layer was extracted with CH$_2$Cl$_2$. The separated organic layer was dried (MgSO$_4$), filtered and the solvent evaporated. The residue was purified by column chromatography over silica gel (eluent: CH$_2$Cl$_2$/CH$_3$OH from 100/0 to 90/10). The product fractions were collected and the solvent was evaporated. Yield: 0.749 g of final compound 5 (58%).

Example B4 a. Preparation of Final Compound 6

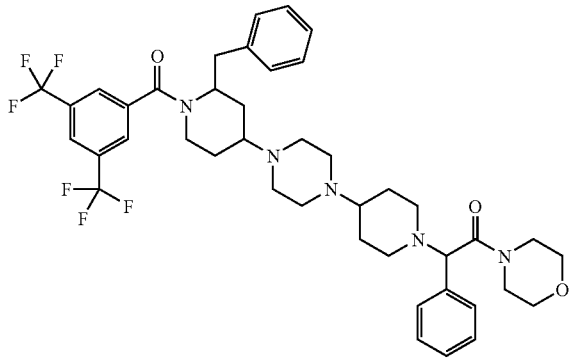

A mixture of final compound 2 (prepared according to B1b) (0.005 mol), 4-(chlorophenylacetyl)-morpholine (0.005 mol) and Na$_2$CO$_3$ (0.01 mol) in MIK, p.a. (125 ml) was stirred and refluxed for 18 hours using a water separator. The reaction mixture was washed with water, dried, filtered and the solvent evaporated. The residue was purified over silica gel on a glass filter (eluent: CH$_2$Cl$_2$/(CH$_3$OH/NH$_3$) 95/5). The product fractions were collected and the solvent was evaporated. The residue was suspended in DIPE, filtered off and dried. Yield: 1.702 g of final compound 6.

b. Preparation of Final Compound 7

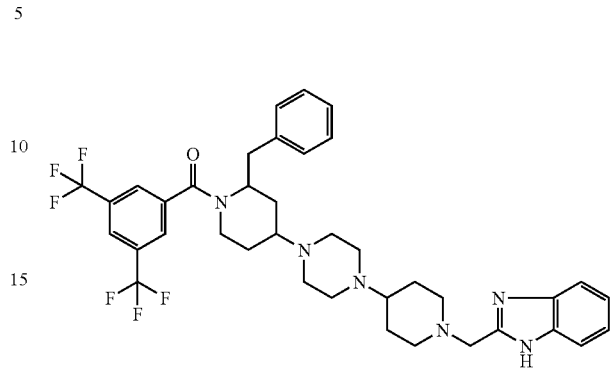

A mixture of final compound 2 (prepared according to B1b) (0.0012 mol), 2-(chloromethyl)-1H-benzimidazole (0.0014 mol) and K$_2$CO$_3$ (0.0018 mol) in CH$_3$CN (5 ml) was stirred and refluxed for 12 hours, then cooled to room temperature and the solvent was evaporated. The residue was taken up in CH$_2$Cl$_2$. The organic layer was washed with H$_2$O, dried (MgSO$_4$), filtered and the solvent was evaporated. The residue (0.95 g) was purified by column chromatography over silica gel (eluent: CH$_2$Cl$_2$/CH$_3$OH/NH$_4$OH 90/10/0.5; 15-40 μm). The pure fractions were collected and the solvent was evaporated. The residue (0.14 g) was crystallized from DIPE. The precipitate was filtered off and dried. Yielding: 0.087 g of final compound 7 (10%) (mp. 135° C.).

c. Preparation of Final Compound 8

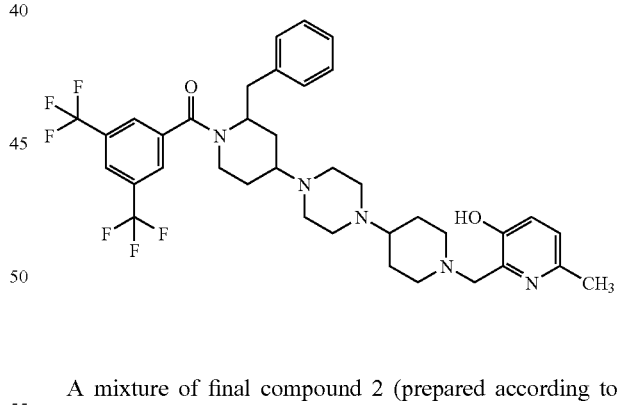

A mixture of final compound 2 (prepared according to B1b) (0.005 mol) and 2-(chloromethyl)-6-methyl-3-pyridinol (0.006 mol) was taken up in DMF (50 ml). N-methyl-N-(1-methylethyl)-propanamine (0.02 mol) was added. The reaction mixture was stirred overnight at ±65° C. The solvent was evaporated. The residue was taken up in CH$_2$Cl$_2$ and washed with a diluted NH$_3$ solution. The separated organic layer was dried, filtered and the solvent was evaporated. The residue was purified by column chromatography over silica gel (eluent: CH$_2$Cl$_2$/(MeOH/NH$_3$) 95/5). The desired fractions were collected and the solvent was evaporated. The residue was suspended in DIPE. The precipitate was filtered off and dried. Yield: 1.423 g of final compound 8.

Example B5

Preparation of Final Compound 9

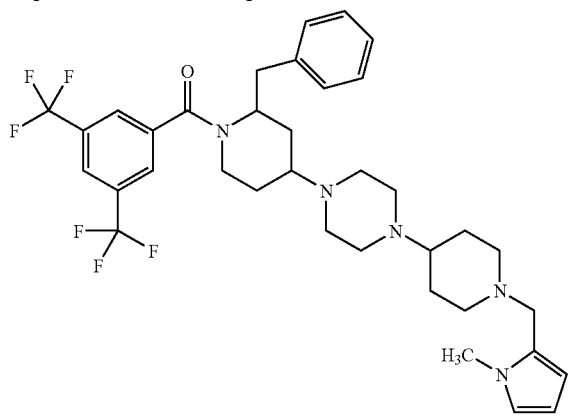

A mixture of final compound 2 (prepared according to B1b) (0.003 mol) and 1-methyl-1H-pyrrole-2-carboxaldehyde (0.0046 mol) was hydrogenated at 50° C. under $H_2$ with Pd/C 10% (1 g) as a catalyst in the presence of thiophene solution (1 ml). After uptake of $H_2$ (1 equiv.), the catalyst was filtered off and the filtrate was evaporated. The residue was purified by column chromatography over silica gel (eluent: $CH_2Cl_2$/(MeOH/$NH_3$) 97/3;95/5). The product fractions were collected and the solvent was evaporated. The residue was suspended in petroleumether. Yield: 1.079 g of final compound 9.

Example B6

Preparation of final Compound 10 and 11

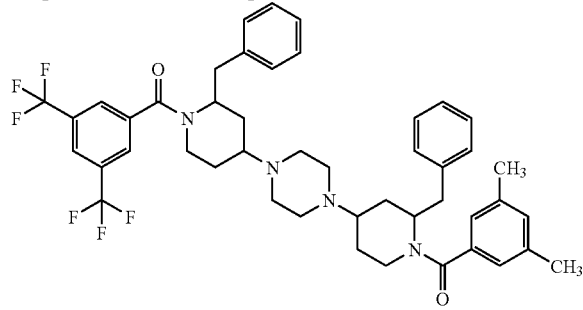

[2α,4α(2R*,4S*)]=compound 10
[2α,4β(2R*,4S*)]=compound 11

A mixture of intermediate compound 2 (prepared according to A1b) (0.005 mol), intermediate compound 11 (prepared according to A3f) (0.005 mol) and Ti(OiPro)$_4$ (3 g) in methanol (150 ml) was hydrogenated at 50° C. under $N_2$ flow with Pd/C 10% (1 g) as a catalyst in the presence of thiophene solution (1 ml). After uptake of $H_2$ (1 equiv), the catalyst was filtered off and the filtrate was evaporated. The residue was taken up in $H_2O$ and $CH_2Cl_2$. The mixture was stirred for 10 min and filtered over dicalite. The organic layer was separated, dried, filtered and the solvent was evaporated. The residue was purified by column chromatography over silica gel (eluent: $CH_2Cl_2$/($CH_3OH$/$NH_3$) 97/3). Two fractions were collected and their solvents were evaporated. Yielding: 0.53 g compound 10 and 0.4 g of final compound 11.

Example B7

Preparation of Final Compound 12

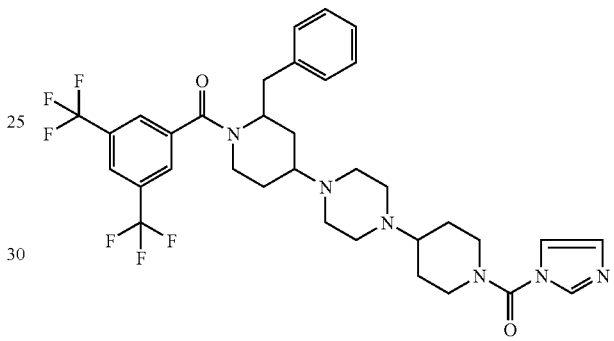

A mixture of final compound 2 (prepared according to B1b) (0.001 mol) in $CH_2Cl_2$ (50 ml) and CDI (0.0015 mol) was stirred overnight. The reaction mixture was washed with diluted NaOH, washed with $H_2O$, dried and the solvent was evaporated. The residue was purified by column chromatography over silica gel (Eluent: $CH_2Cl_2$/$CH_3OH$ 100/0 and 90/10). The product fractions were collected and the solvent evaporated. Yield: 0.645 g of final compound 12.

Example B8

Preparation of Final Compound 13

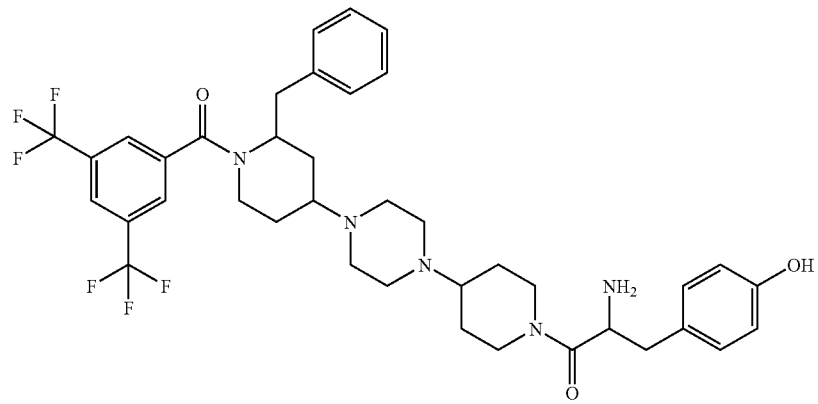

A mixture of intermediate compound 5 (prepared according to A2) (0.0015 mol) in HCl/2-propanol (5 ml) and methanol (20 ml) was stirred and refluxed for 1 hour. The reaction mixture was crystallized, filtered off and dried. Yield: 0.43 g of final compound 13 (38%)

Example B9

Preparation of Final Compound 40

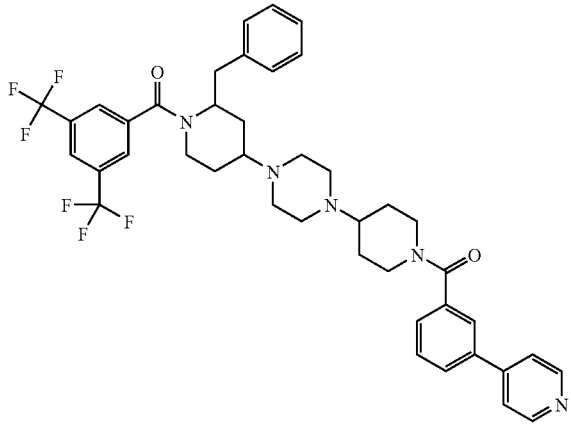

A mixture of final compound 31 (prepared according to B2)(0.065 mmol), 4-pyridinyl-boronic acid (0.09 mmol), Pd(OAc)$_2$ (0.015 mmol), 1,3-bis(diphenylphosphino)propane (0.03 mmol), Na$_2$CO$_3$, 2M (1 ml) and DME (2 ml) was stirred at 100° C. for 16 hours. The solvent was evaporated and the residue was taken up in H$_2$O and extracted with CH$_2$Cl$_2$. The organic layer was separated, dried with MgSO$_4$ and the solvent evaporated. The residue was purified by column chromatography over kromasil (gradient: CH$_2$Cl$_2$/CH$_3$OH 95/5). The desired fractions were collected and the solvent was evaporated. Yield: 1 mg of final compound 40.

Example B10

Preparation of Final Compound 85

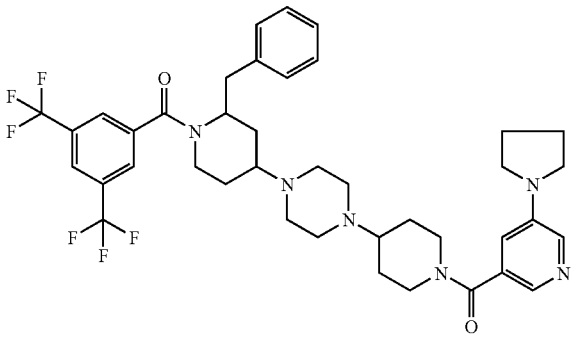

A mixture of final compound 83 (prepared according to B2)(0.0004 mol), pyrrolidine (0.0006 mol), Pd$_2$(dba)$_3$ (0.00001 mol), BINAP (0.00003 mol) and 2-methyl-2-propanol sodium salt (0.0006 mol) in toluene (5 ml) was stirred at 100° C. for 16 hours. The solvent was evaporated and the residue was taken up in H$_2$O and extracted with CH$_2$Cl$_2$. The organic layer was separated, dried with MgSO$_4$ and the solvent evaporated. The residue was purified by column chromatography over kromasil (gradient: CH$_2$Cl$_2$/CH$_3$OH 95/5). The desired fractions were collected and the solvent was evaporated. Yield: 0.119 g of final compound 85.

Example B11

Preparation of Final Compound 43

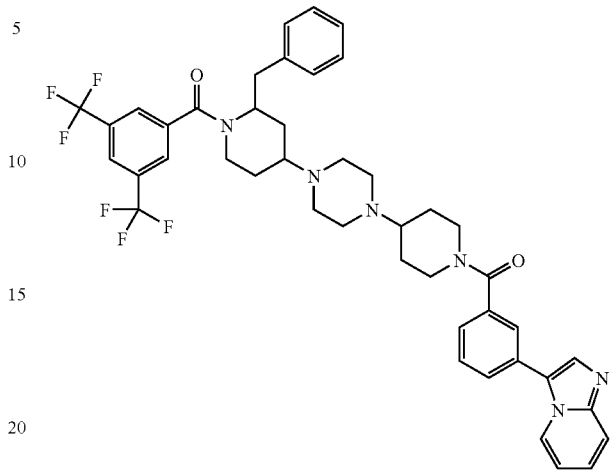

A mixture of final compound 31 (prepared according to B2)(0.065 mmol), imidazo(1,2-a)pyridine (0.09 mmol), Pd(OAc)$_2$ (0.015 mmol), 1,3-bis(diphenylphosphino)propane (0.03 mmol) and Cs$_2$CO$_3$ (0.09 mmol) in NMP (5 ml) was stirred at 140° C. for 16 hours. The solvent was evaporated and the residue was taken up in H$_2$O and extracted with CH$_2$Cl$_2$. The organic layer was separated, dried with MgSO$_4$ and the solvent evaporated. The residue was purified by column chromatography over kromasil (gradient: CH$_2$Cl$_2$/CH$_3$OH 95/5). The desired fractions were collected and the solvent was evaporated. The desired fractions were collected and the solvent was evaporated. Yield: 8 mg of final compound 43.

Example B12

Preparation of Final Compound 44

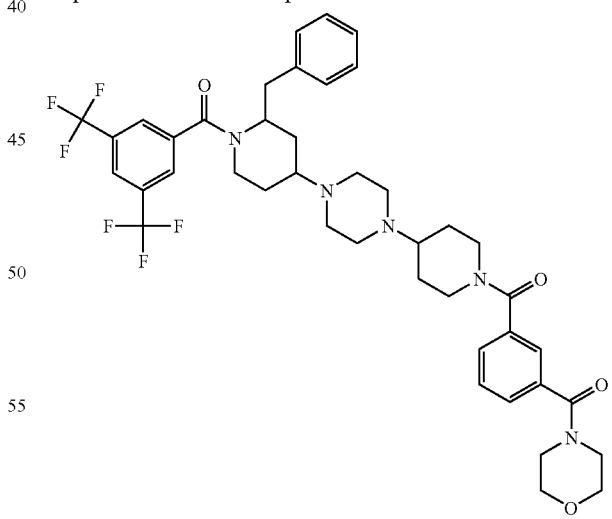

A mixture of compound 31 (prepared according to B2) (0.065 mmol), morpholine (0.2 mmol), Pd(OAc)$_2$ (0.015 mmol) and 1,3-bis(diphenylphosphino)propane (0.03 mmol) in diglyme (3 ml) under 1 atmosphere CO was stirred at 150° C. for 16 hours. The solvent was evaporated and the residue was taken up in H$_2$O and extracted with CH$_2$Cl$_2$. The organic layer was separated, dried with MgSO$_4$ and the solvent evaporated. The residue was purified by column chromatography over kromasil (gradient: CH$_2$Cl$_2$/CH$_3$OH 95/5). The desired fractions were collected and the solvent was evaporated. The desired fractions were collected and the solvent was evaporated. Yield: 3 mg of final compound 44.

Example B13

Preparation of Final Compound 144

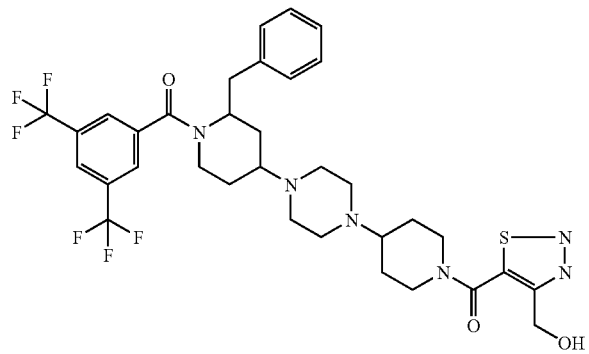

A mixture of 4-[(4-acetyloxy)methyl]-1,2,3-thiadiazole-5-carboxylic acid methyl ester (0.001 mol), final compound 2 (prepared according to B1b) (0.002 mol), NaCN (20 mg) in methanol (20 ml) was stirred and refluxed for 20 hours. The solvent was evaporated and the residue was purified by column chromatography over silica gel (eluent: CH$_2$Cl$_2$/MeOH from 100/0 to 80/20). The desired fractions were collected and the solvent was evaporated. The residue was suspended in petroleum ether. The precipitate was filtered off and dried. Yield: 0.110 g of final compound 144.

Example B14

Preparation of Final Compound 130

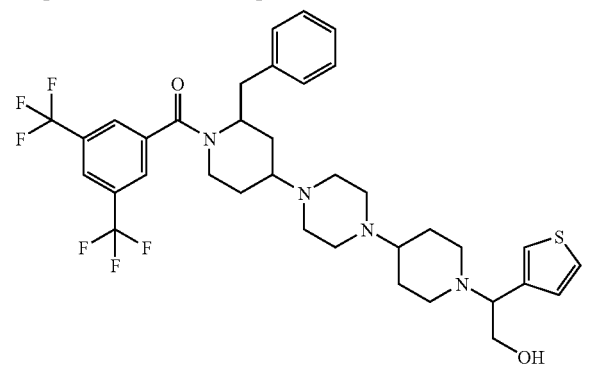

A mixture of final compound 2 (prepared according to B1b) (0.001 mol), glycolaldehyde dimer (0.001 mol) and 3-thiophene boronic acid (0.001 mol) in 2,2,2-trifluoroethanol (5 ml) was stirred at room temperature for 18 hours. This was followed by addition of a solution of K$_2$CO$_3$ (10%) and extraction with ethyl acetate. The combined organic layers were dried (MgSO$_4$), filtered and concentrated under vacuum. The residue (0.6 g) was purified by chromatography on a silicagel column (CH$_2$Cl$_2$/MeOH/NH$_4$OH 92/08/0.2) and the product fractions were concentrated, providing 0.29 g (47%) of final compound 130.

Example B15

Preparation of Final Compound 153

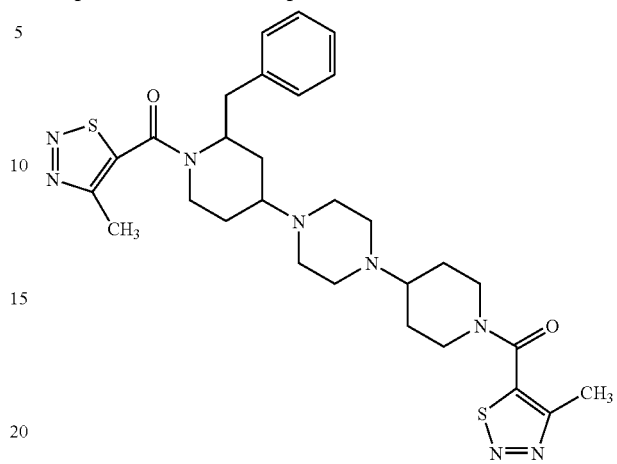

A mixture of intermediate compound 12 (prepared according to A4) (0.00934 mol) and Et$_3$N (0.02 mol) in CH$_2$Cl$_2$ (200 ml) was stirred on an ice bath, then a solution of 4-methyl-1,2,3-thiadiazole-5-carbonyl chloride (0.00943 mol) in CH$_2$Cl$_2$ (20 ml) was added dropwise over 15 minutes at 0° C. The reaction mixture allowed to reach room temperature and was stirred for 1 hour at room temperature, NaOH (20 ml) was added and the reaction mixture was stirred for 15 minutes at room temperature. The layers were separated and the aqueous layer was extracted with CH$_2$Cl$_2$. The organic layer was washed with H$_2$O, dried (MgSO$_4$), filtered off and the solvent was evaporated. The residue was purified by column chromatography over silicagel (eluent: CH$_2$Cl$_2$/MeOH/(MeOH/ NH$_3$) from 100/0/0 to 90/10/0 to 90/10/0). Two product fractions were collected and each solvent was evaporated. Yield fraction 1: 1.260 g of final compound 153 (22%).

The compounds exemplified in the following tables were prepared in a manner analogous to one of the foregoing examples B1 to B15.

Analytical Data

For a number of compounds, either melting points, LCMS data or optical rotations were recorded.

Melting Point

If possible, melting points (or ranges) were obtained with a Büchi melting point apparatus B-545. The heating medium is a metal block. The melting of the sample is visually observed by a magnifying lens and a big light contrast. Melting points are measured with a temperature gradient of either 3 or 10 degrees Celsius/minute.

| Compound no. | Result (° C.) |
|---|---|
| 1 | 115.9-119.7 |
| 2 | 160.6-163.2 |
| 3 | 149.9-151.7 |
| 4 | 180.5-182.1 |
| 5 | 87.8-121.4 |
| 6 | 87.7-111.2 |
| 7 | 141.0-177.3 |
| 8 | 162.3-164.3 |
| 9 | 122.1-123.8 |
| 10 | 97.0-120.4 |
| 11 | 111.9-125.4 |
| 12 | 66.7-79.0 |
| 13 | 284.5-288.6 |

-continued

| Compound no. | Result (° C.) |
|---|---|
| 14 | 107.4-116.1 |
| 15 | 188.1-190.3 |
| 19 | 140.3-144.8 |
| 22 | 98.3-119.9 |
| 29 | 142.9-146.5 |
| 31 | 153.1-155.2 |
| 32 | 83.3-95.5 |
| 33 | 82.7-98.6 |
| 34 | 80.7-95.5 |
| 37 | 298.1-319.7 |
| 38 | 83.2-110.2 |
| 39 | 279.4-280.9 |
| 46 | 81.3-107.2 |
| 49 | 145.3-149.6 |
| 50 | 92.1-100.7 |
| 51 | 108.9-127.3 |
| 52 | 93.9-104.6 |
| 53 | 156.6-161.0 |
| 54 | 107.6-122.2 |
| 55 | 96.7-106.3 |
| 56 | 171.3-181.5 |
| 57 | 167.4-169.4 |
| 58 | 92.5-102.6 |
| 59 | 79.1-98.2 |
| 60 | 100.5-121.4 |
| 62 | 91.4-120.3 |
| 63 | 86.0-99.4 |
| 64 | 133.6-159.5 |
| 65 | 102.3-105.8 |
| 69 | 108.6-120.6 |
| 71 | 93.5-127.3 |
| 72 | 91.6-103.2 |
| 73 | 100.5-110.5 |
| 75 | 78.8-93.8 |
| 76 | 76.2-93.8 |
| 77 | 273.6-295.2 |
| 79 | 74.3-100.3 |
| 80 | 106.7-126.1 |
| 81 | 85.3-120.6 |
| 82 | 91.9-121.2 |
| 83 | 86.9-102.1 |
| 84 | 92.2-126.1 |
| 85 | 145.4-147.2 |
| 88 | 70.6-108.7 |
| 89 | 96.1-109.4 |
| 90 | 111.9-120.1 |
| 91 | 91.5-108.1 |
| 92 | 100.7-117.9 |
| 93 | 184.1-192.4 |
| 98 | 177.1-180.6 |
| 99 | 65.9-83.0 |
| 100 | 76.1-100.1 |
| 102 | 72.9-93.5 |
| 103 | 83.7-100.8 |
| 104 | 105.1-108.5 |
| 106 | 77.2-99.1 |
| 108 | 314.8-335.8 |
| 109 | 95.4-107.7 |
| 110 | 84.6-111.8 |
| 111 | 87.3-109.3 |
| 113 | 252.3-291.7 |
| 116 | 102.8-125.6 |
| 117 | 158.2-160.5 |
| 122 | 177.5° c. |

LCMS Conditions

The HPLC gradient was supplied by a Waters Alliance HT 2790 system with a columnheater set at 40° C. Flow from the column was split to a Waters 996 photodiode array (PDA) detector and a Waters-Micromass ZQ mass spectrometer with an electrospray ionization source operated in positive and negative ionization mode. Reversed phase HPLC was carried out on a Xterra MS C18 column (3.5 mm, 4.6×100 mm) with a flow rate of 1.6 ml/min. Three mobile phases (mobile phase A 95% 25 mM ammoniumacetate+5% acetonitrile; mobile phase B: acetonitrile; mobile phase C: methanol) were employed to run a gradient condition from 100% A to 50% B and 50% C in 6.5 min., to 100% B in 1 min, 100% B for 1 min. and reequilibrate with 100% A for 1.5 min. An injection volume of 10 mL was used.

Mass spectra were acquired by scanning from 100 to 1000 in 1 s using a dwell time of 0.1 s. The capillary needle voltage was 3 kV and the source temperature was maintained at 140° C. Nitrogen was used a the nebulizer gas. Cone voltage was 10 V for positive ionzation mode and 20 V for negative ionization mode. Data acquisition was performed with a Waters-Micromass MassLynx-Openlynx data system.

| Compound no. | LCMS MS (MH+) |
|---|---|
| 16 | 661 |
| 18 | 703 |
| 20 | 711 |
| 21 | 724 |
| 22 | 701 |
| 23 | 703 |
| 24 | 753 |
| 26 | 809 |
| 27 | 699 |
| 28 | 749 |
| 30 | 654 |
| 35 | 703 |
| 36 | 703 |
| 42 | 756 |
| 48 | 719 |
| 61 | 747 |
| 70 | 693 |
| 74 | 692 |
| 94 | 740 |
| 96 | 703 |
| 101 | 651 |
| 105 | 731 |
| 107 | 691 |
| 114 | 803 |
| 115 | 791 |
| 118 | 859 |
| 119 | 767 |
| 124 | 700 |
| 125 | 673 |
| 126 | 673 |
| 127 | 673 |
| 128 | 737 |
| 129 | 709 |
| 130 | 709 |
| 131 | 693 |
| 132 | 687 |
| 133 | 687 |
| 134 | 687 |
| 135 | 701 |
| 136 | 677 |
| 137 | 677 |
| 138 | 677 |
| 139 | 709 |
| 140 | 709 |
| 141 | 709 |
| 142 | 709 |
| 143 | 709 |
| 144 | 725 |
| 145 | 681 |
| 146 | 681 |
| 147 | 681 |
| 148 | 651 |
| 149 | 651 |
| 150 | 651 |
| 151 | 677 |
| 153 | 595 |
| 154 | 709 |
| 155 | 709 |
| 156 | 619 |
| 157 | 723 |
| 158 | 745 |

Optical Rotations

Optical rotations were recorded on a polarimeter (Perkin Elmer) at 20° C. Specifics on concentration, wavelength and solvent are given in the table.

| Compound no. | [α] | Wavelength (nm) | Concentration (w/v %) | Solvent |
|---|---|---|---|---|
| 18 | −33.77° | 365 | 0.4086 | CH$_3$OH |
| 159 | −35.56° | 365 | 0.4302 | CH$_3$OH |
| 160 | −33.66° | 365 | 0.5288 | CH$_3$OH |
| 161 | −34.75° | 365 | 0.4058 | CH$_3$OH |
| 162 | −6.72° | 436 | 0.6400 | CH$_3$OH |
| 163 | −33.2° | 365 | 0.4638 | CH$_3$OH |
| 164 | −34.1° | 365 | 0.4340 | CH$_3$OH |
| 165 | −34.43° | 365 | 0.4298 | CH$_3$OH |
| 166 | −33.95° | 365 | 0.4094 | CH$_3$OH |
| 167 | −29.91° | 365 | 0.4848 | CH$_3$OH |
| 168 | −29.12° | 365 | 0.4602 | CH$_3$OH |
| 169 | −32.32° | 365 | 0.4548 | CH$_3$OH |
| 170 | −33.3° | 365 | 0.4354 | CH$_3$OH |
| 171 | −35.06° | 365 | 0.4164 | CH$_3$OH |
| 172 | −35.84° | 365 | 0.4380 | CH$_3$OH |
| 173 | −34.53° | 365 | 0.4054 | CH$_3$OH |

TABLE 1

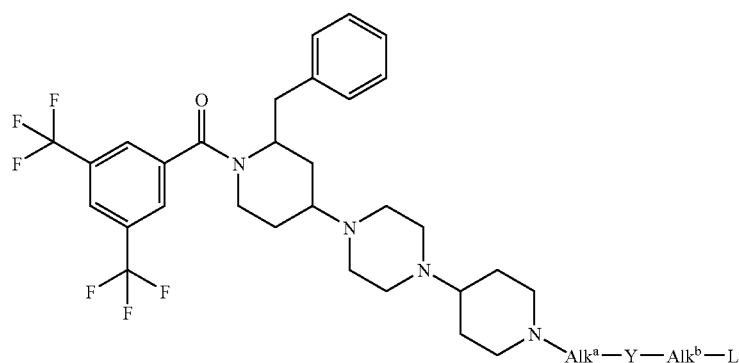

| Comp. No. | Exp. No. | Alk$^a$ | Y | Alk$^b$ | L | Physical data |
|---|---|---|---|---|---|---|
| 2 | B1b | cb | cb | cb | H | 2R-trans |
| 121 | B1b | cb | cb | cb | H | 2R-cis |
| 122 | B1b | cb | cb | cb | H | 2S-trans |
| 123 | B1b | cb | cb | cb | H | 2S-cis |
| 15 | B4b | cb | cb | cb | 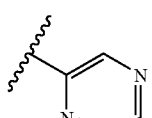 | 2R-trans |
| 16 | B4a | cb | cb | cb | 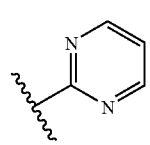 | 2R-trans |
| 17 | B4c | cb | cb | ob | 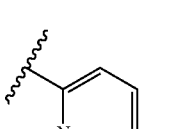 | 2R-trans |
| 18 | B4c | cb | cb | cb | 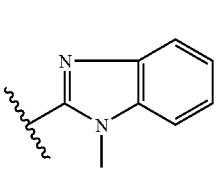 | 2R-trans |

TABLE 1-continued

| Comp. No. | Exp. No. | Alk^a | Y | Alk^b | L | Physical data |
|---|---|---|---|---|---|---|
| 124 | B4c | cb | cb | cb | benzisoxazol-3-yl | 2R-trans |
| 9 | B5 | —CH$_2$— | cb | cb | 1-methylpyrrol-2-yl | 2R-trans |
| 20 | B4b | —CH$_2$— | cb | cb | 4-chloro-1-methylimidazol-2-yl | 2R-trans |
| 8 | B4c | —CH$_2$— | cb | cb | 3-hydroxy-6-methylpyridin-2-yl | 2R-trans |
| 7 | B4b | —CH$_2$— | cb | cb | 1H-benzimidazol-2-yl | 2R-trans |
| 21 | B4b | —CH$_2$— | cb | cb | quinolin-2-yl | B-trans |
| 125 | B1a | —CH$_2$— | cb | cb | phenyl | 2R-cis |
| 126 | B1a | —CH$_2$— | cb | cb | phenyl | 2S-cis |

TABLE 1-continued

| Comp. No. | Exp. No. | Alk$^a$ | Y | Alk$^b$ | L | Physical data |
|---|---|---|---|---|---|---|
| 1 | B1a | —CH$_2$— | cb | cb | phenyl | 2R-trans |
| 127 | B1a | —CH$_2$— | cb | cb | phenyl | 2S-trans |
| 22 | B4b | —CH$_2$— | cb | cb | 3,5-dimethylphenyl | 2R-trans |
| 23 | B4b | —CH$_2$— | cb | cb | 2-methoxyphenyl | 2R-trans |
| 24 | B4b | —CH$_2$— | cb | cb | 1-(2-methylphenyl)-1H-imidazol-5-yl | 2R-trans |
| 25 | B4b | —CH$_2$— | cb | cb | 1-(1-phenylethyl)-1H-imidazol-5-yl | B-trans |

TABLE 1-continued

| Comp. No. | Exp. No. | Alk^a | Y | Alk^b | L | Physical data |
|---|---|---|---|---|---|---|
| 26 | B4b | —CH₂— | cb | cb | 3,5-bis(trifluoromethyl)phenyl | B-trans |
| 27 | B4b | —CH₂—CH=CH— | cb | cb | phenyl | [2B-[2α,4β(E)] |
| 128 | B14 | HO-CH₂-CH(—)(—) | cb | cb | 2-chlorophenyl | 2R-trans |
| 129 | B14 | HO-CH₂-CH(—)(—) | cb | cb | 2-thienyl | 2R-trans |
| 130 | B14 | HO-CH₂-CH(—)(—) | cb | cb | 3-thienyl | 2R-trans |
| 131 | B14 | HO-CH₂-CH(—)(—) | cb | cb | 2-furyl | 2R-trans |
| 28 | B4c | PhCH(—)(—) | cb | cb | phenyl | B-trans |

TABLE 1-continued
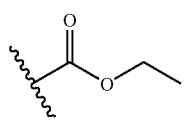
| Comp. No. | Exp. No. | Alk$^a$ | Y | Alk$^b$ | L | Physical data |
|---|---|---|---|---|---|---|
| 29 | B2 | cb | C=O | cb | 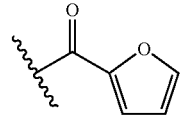 | 2R-trans |
| 162 | B3b | cb | C=O | cb | 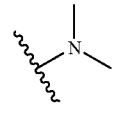 | 2R-trans |
| 30 | B2 | cb | C=O | cb | 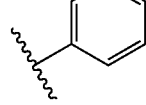 | 2R-trans |
| 3 | B2 | cb | C=O | cb | 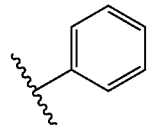 | 2R-trans mp. 142.5° C. |
| 132 | B2 | cb | C=O | cb | | 2S-trans |
| 133 | B2 | cb | C=O | cb | 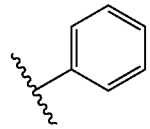 | 2R-cis |
| 134 | B2 | cb | C=O | cb | 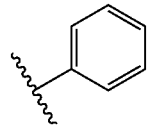 | 2S-cis |
| 31 | B2 | cb | C=O | cb | 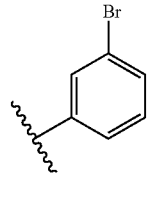 | 2R-trans |

TABLE 1-continued
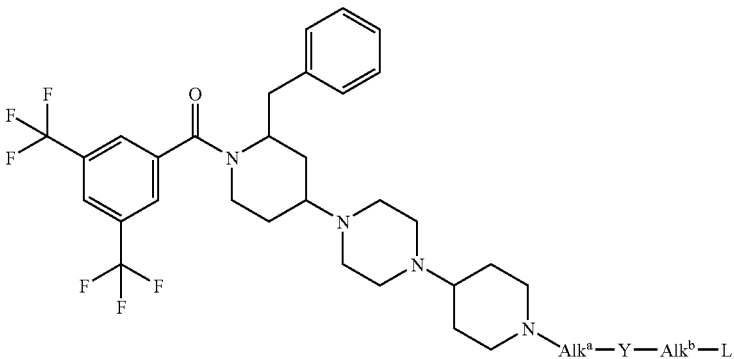
| Comp. No. | Exp. No. | Alk$^a$ | Y | Alk$^b$ | L | Physical data |
|---|---|---|---|---|---|---|
| 32 | B2 | cb | C=O | cb | 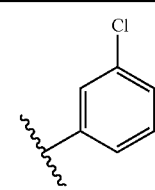 3-Cl-phenyl | 2R-trans |
| 165 | B2 | cb | C=O | cb | 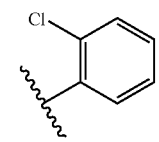 2-Cl-phenyl | 2R-trans |
| 33 | B2 | cb | C=O | cb | 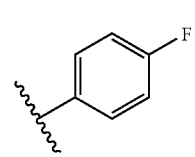 4-F-phenyl | 2R-trans |
| 34 | B2 | cb | C=O | cb | 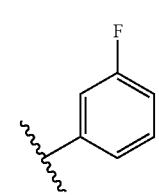 3-F-phenyl | 2R-trans |
| 164 | B2 | cb | C=O | cb | 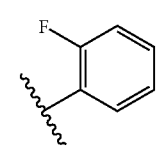 2-F-phenyl | 2R-trans |
| 35 | B3b | cb | C=O | cb | 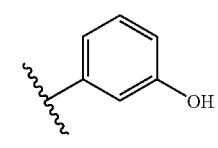 3-OH-phenyl | 2R-trans |
| 36 | B2 | cb | C=O | cb | 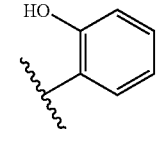 2-OH-phenyl | 2R-trans |

TABLE 1-continued

| Comp. No. | Exp. No. | Alk$^a$ | Y | Alk$^b$ | L | Physical data |
|---|---|---|---|---|---|---|
| 163 | B2 | cb | C=O | cb | 2-methylphenyl | 2R-trans |
| 37 | B2 | cb | C=O | cb | 3-methylphenyl | 2R-trans |
| 135 | B2 | cb | C=O | cb | 3-methylphenyl | 2R-trans HCl(1:2) |
| 38 | B2 | cb | C=O | cb | 3-(trifluoromethyl)phenyl | 2R-trans |
| 39 | B3a | cb | C=O | cb | 3-cyanophenyl | 2R-trans |
| 40 | B9 | cb | C=O | cb | 3-(pyridin-4-yl)phenyl | 2R-trans |
| 41 | B10 | cb | C=O | cb | 3-(morpholin-4-yl)phenyl | 2R-trans |

TABLE 1-continued

| Comp. No. | Exp. No. | Alk<sup>a</sup> | Y | Alk<sup>b</sup> | L | Physical data |
|---|---|---|---|---|---|---|
| 42 | B10 | cb | C=O | cb | 3-(pyrrolidin-1-yl)phenyl | 2R-trans |
| 43 | B11 | cb | C=O | cb | 3-(imidazo[1,2-a]pyridin-3-yl)phenyl | 2R-trans |
| 44 | B12 | cb | C=O | cb | 3-(morpholine-4-carbonyl)phenyl | 2R-trans |
| 45 | B12 | cb | C=O | cb | 3-(pyrrolidine-1-carbonyl)phenyl | 2R-trans |
| 46 | B2 | cb | C=O | cb | 3-isopropoxyphenyl | B-trans |
| 47 | B2 | cb | C=O | cb | 4-fluoro-3-methylphenyl | 2R-trans |
| 48 | B2 | cb | C=O | cb | 2-fluoro-5-methylphenyl | 2R-trans |

TABLE 1-continued

| Comp. No. | Exp. No. | Alk$^a$ | Y | Alk$^b$ | L | Physical data |
|---|---|---|---|---|---|---|
| 49 | B2 | cb | C=O | cb | 3,4-difluorophenyl | 2R-trans |
| 50 | B2 | cb | C=O | cb | 2,4-difluorophenyl | 2R-trans |
| 51 | B2 | cb | C=O | cb | 3,5-difluorophenyl | 2R-trans |
| 52 | B2 | cb | C=O | cb | 2,5-difluorophenyl | 2R-trans |
| 53 | B2 | cb | C=O | cb | 3-chloro-4-fluorophenyl | 2R-trans |
| 54 | B2 | cb | C=O | cb | 2-methoxy-5-chlorophenyl | 2R-trans |

TABLE 1-continued
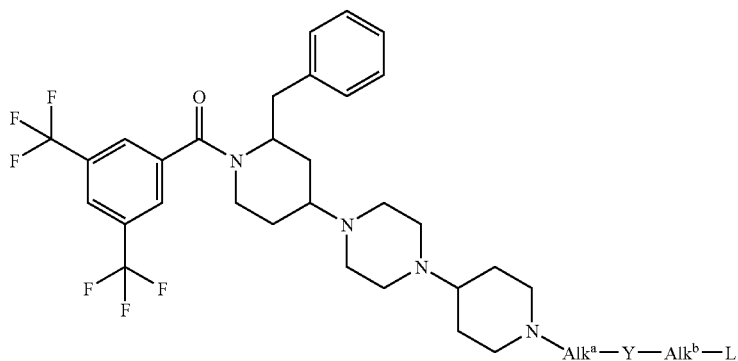
| Comp. No. | Exp. No. | Alk$^a$ | Y | Alk$^b$ | L | Physical data |
|---|---|---|---|---|---|---|
| 55 | B2 | cb | C=O | cb | 3,5-dichlorophenyl | 2R-trans |
| 56 | B3b | cb | C=O | cb | 2-hydroxy-5-methylphenyl | 2R-trans |
| 57 | B2 | cb | C=O | cb | 3,5-bis(trifluoromethyl)phenyl | B-trans |
| 58 | B2 | cb | C=O | cb | 3,5-dimethylphenyl | 2R-cis |
| 59 | B2 | cb | C=O | cb | 3,5-dimethylphenyl | B-trans |
| 60 | B2 | cb | C=O | cb | 3,5-dimethylphenyl | trans |

TABLE 1-continued

| Comp. No. | Exp. No. | Alk$^a$ | Y | Alk$^b$ | L | Physical data |
|---|---|---|---|---|---|---|
| 170 | B3b | cb | C=O | cb | 2,3-dimethylphenyl | 2R-trans |
| 61 | B2 | cb | C=O | cb | 2,6-dimethoxyphenyl | 2R-trans |
| 62 | B2 | cb | C=O | cb | 2,4,5-trifluorophenyl | 2R-trans |
| 63 | B2 | cb | C=O | cb | 3,4,5-trifluorophenyl | 2R-trans |
| 64 | B3a | cb | C=O | cb | 4-amino-2-chloro-5-methoxyphenyl | 2R-trans |
| 65 | B2 | cb | C=O | cb | 3,4,5-trimethoxyphenyl | 2R-trans |

TABLE 1-continued
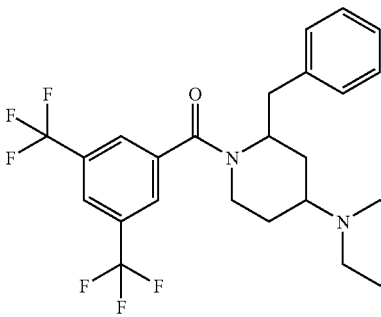
| Comp. No. | Exp. No. | Alk$^a$ | Y | Alk$^b$ | L | Physical data |
|---|---|---|---|---|---|---|
| 66 | B2 | cb | C=O | cb | 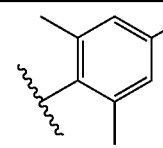 | B-trans |
| 67 | B3b | cb | C=O | eb | 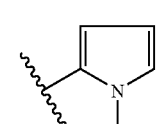 | 2R-trans |
| 68 | B2 | cb | C=O | cb | 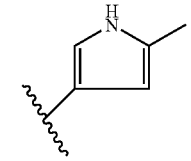 | 2R-trans |
| 69 | B3a | cb | C=O | cb | 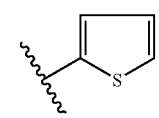 | 2R-trans |
| 5 | B3b | cb | C=O | cb | 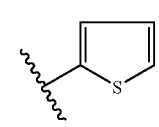 | 2R-trans |
| 70 | B2 | cb | C=O | cb | 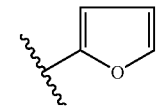 | 2R-trans |
| 161 | B2 | cb | C=O | cb | 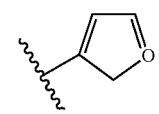 | 2R-trans |
| 71 | B3a | cb | C=O | cb | | 2R-trans |

TABLE 1-continued

| Comp. No. | Exp. No. | Alk{a} | Y | Alk{b} | L | Physical data |
|---|---|---|---|---|---|---|
| 136 | B3b | cb | C=O | cb | 3-furanyl (dihydro) | 2S-trans |
| 137 | B3b | cb | C=O | cb | 3-furanyl (dihydro) | 2R-cis |
| 138 | B3b | cb | C=O | cb | 3-furanyl (dihydro) | 2S-cis |
| 72 | B3a | cb | C=O | cb | 2,5-dimethyl-3-furanyl | 2R-trans |
| 12 | B7 | cb | C=O | cb | 1-imidazolyl | 2R-trans |
| 73 | B2 | cb | C=O | cb | 1-tert-butyl-3,5-dimethylpyrazol-4-yl | 2R-trans |
| 19 | B2 | cb | C=O | cb | 1,3-dimethylpyrazol-5-yl | 2R-trans |
| 74 | B2 | cb | C=O | cb | 5-methylisoxazol-3-yl | 2R-trans |

TABLE 1-continued

| Comp. No. | Exp. No. | Alk<sup>a</sup> | Y | Alk<sup>b</sup> | L | Physical data |
|---|---|---|---|---|---|---|
| 75 | B2 | cb | C=O | cb | 3,5-dimethylisoxazol-4-yl | 2R-trans |
| 4 | B3a | cb | C=O | cb | 5-methylisoxazol-4-yl | 2R-trans |
| 76 | B3a | cb | C=O | cb | 2,4-dimethylthiazol-5-yl | 2R-trans |
| 77 | B2 | cb | C=O | cb | 4-methyl-1,2,3-thiadiazol-5-yl | 2R-trans m.p. 119.6° C. |
| 139 | B2 | eb | C=O | cb | 4-methyl-1,2,3-thiadiazol-5-yl | 2R-cis |
| 140 | B2 | cb | C=O | cb | 4-methyl-1,2,3-thiadiazol-5-yl | 2S-cis |
| 141 | B2 | cb | C=O | cb | 4-methyl-1,2,3-thiadiazol-5-yl | 2S-trans |
| 78 | B2 | cb | C=O | cb | 4-methyl-1,2,3-thiadiazol-5-yl | 2R-trans; HCl(1:2); H<sub>2</sub>O(1:1) |

TABLE 1-continued
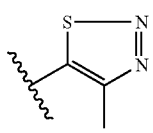
| Comp. No. | Exp. No. | Alk<sup>a</sup> | Y | Alk<sup>b</sup> | L | Physical data |
|---|---|---|---|---|---|---|
| 142 | B2 | cb | C=O | cb | 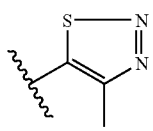 | 2R-trans; succinate(1:2) |
| 143 | B2 | cb | C=O | cb | 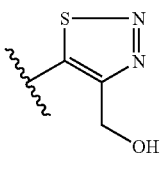 | 2R-trans; malonate(1:2) |
| 144 | B13 | cb | C=O | cb | 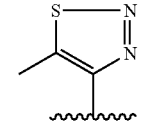 | 2R-trans |
| 120 | B3b | cb | C=O | cb | 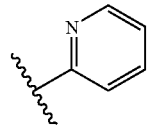 | 2R-trans |
| 79 | B2 | cb | C=O | cb | 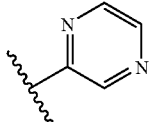 | 2R-trans |
| 166 | B3b | cb | C=O | cb | 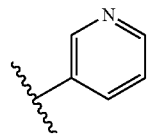 | 2R-trans |
| 80 | B2 | cb | C=O | cb | 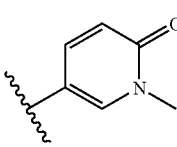 | 2R-trans |
| 81 | B3b | cb | C=O | cb |  | 2R-trans |

TABLE 1-continued
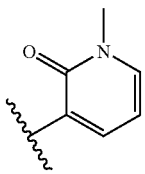
| Comp. No. | Exp. No. | Alk<sup>a</sup> | Y | Alk<sup>b</sup> | L | Physical data |
|---|---|---|---|---|---|---|
| 82 | B3b | cb | C=O | cb | 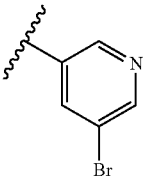 | 2R-trans |
| 83 | B2 | cb | C=O | cb | 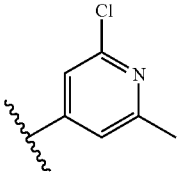 | 2R-trans |
| 14 | B2 | cb | C=O | cb | 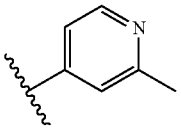 | 2R-trans |
| 84 | B3b | cb | C=O | cb | 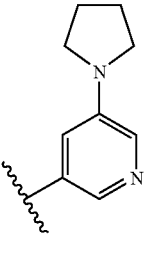 | 2R-trans |
| 85 | B10 | cb | C=O | cb | 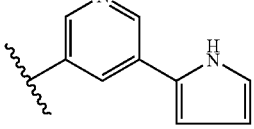 | 2R-trans |
| 86 | B9 | cb | C=O | cb | | 2R-trans |

TABLE 1-continued
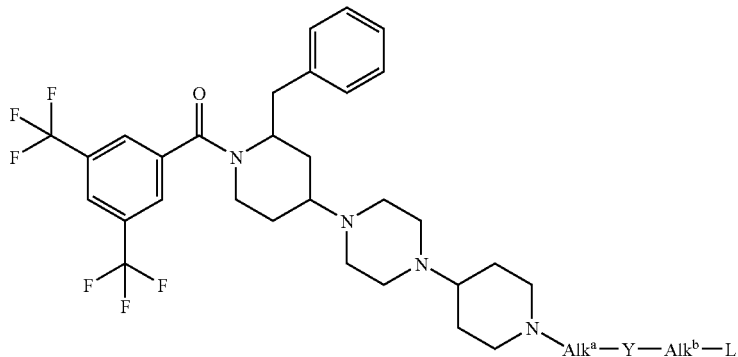
| Comp. No. | Exp. No. | Alk$^a$ | Y | Alk$^b$ | L | Physical data |
|---|---|---|---|---|---|---|
| 87 | B9 | cb | C=O | cb | | 2R-trans |
| 88 | B8 | cb | C=O | cb | | 2R-trans |
| 89 | B3b | cb | C=O | cb | | 2R-trans |
| 90 | B3b | cb | C=O | cb | | [2R-[2α,4β(S)]] |
| 91 | B8 | cb | C=O | cb | | [2R-[2α,4β(S)]] |
| 92 | B2 | cb | C=O | cb | | 2R-trans |

TABLE 1-continued

| Comp. No. | Exp. No. | Alk<sup>a</sup> | Y | Alk<sup>b</sup> | L | Physical data |
|---|---|---|---|---|---|---|
| 93 | B3b | cb | C=O | cb | coumarin-3-yl | 2R-trans |
| 94 | B3b | cb | C=O | cb | 3-(1-methyl-isoindolyl) | B-trans |
| 169 | B3b | cb | C=O | cb | benzothiophen-2-yl | 2R-trans |
| 96 | B2 | cb | C=O | cb | phenoxy | B-trans |
| 145 | B3b | cb | C=O | cb | tetrahydrofuran-3-yl | 2S-trans |
| 146 | B3b | cb | C=O | cb | tetrahydrofuran-3-yl | 2R-cis |
| 147 | B3b | cb | C=O | cb | tetrahydrofuran-3-yl | 2S-cis |
| 173 | | cb | C=O | cb | 5-oxopyrrolidin-2-yl | |

TABLE 1-continued

| Comp. No. | Exp. No. | Alk$^a$ | Y | Alk$^b$ | L | Physical data |
|---|---|---|---|---|---|---|
| 97 | B4c | —CH$_2$— | C=O | cb | 2,6-dimethylphenyl-NH— | 2R-trans |
| 98 | B2 | cb | C=O | —CH$_2$— | —H | 2R-trans |
| 99 | B2 | cb | C=O | isopropylidene | —H | 2R-trans |
| 159 | B2 | cb | C=O | isopropylidene | —H | 2R-trans |
| 167 | B3b | cb | C=O | isopropylidene | —NHC(=O)O-tBu | 2R-trans |
| 160 | B2 | cb | C=O | neopentyl | —H | 2R-trans |
| 100 | B2 | cb | C=O | methylidene | —H | 2R-trans |
| 101 | B2 | cb | C=O | cyclopropyl | —H | 2R-trans |
| 148 | B2 | cb | C=O | cyclopropyl | —H | 2S-trans |
| 149 | B2 | cb | C=O | cyclopropyl | —H | 2R-cis |

TABLE 1-continued

| Comp. No. | Exp. No. | Alk^a | Y | Alk^b | L | Physical data |
|---|---|---|---|---|---|---|
| 150 | B2 | cb | C=O | cyclopropane-1,2-diyl | —H | 2S-cis |
| 171 | B3b | cb | C=O | cyclopropane-1,2-diyl | —H | 2R-trans |
| 172 | B3b | cb | C=O | 1-hydroxycyclopropane-1,2-diyl | —H | 2R-trans |
| 102 | B2 | cb | C=O | cyclobutane-1,3-diyl | —H | 2R-trans |
| 151 | B2 | cb | C=O | cyclopentane-1,3-diyl | —H | 2R-trans |
| 103 | B2 | cb | C=O | cyclohexane-1,4-diyl | —H | 2R-trans |
| 104 | B2 | cb | C=O | —CH$_2$— | —OCH$_3$ | 2R-trans |
| 105 | B2 | cb | C=O | —CH$_2$— | 3-methoxyphenyl | 2R-trans |

TABLE 1-continued
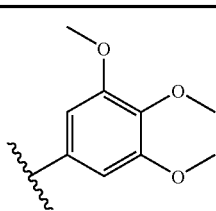
| Comp. No. | Exp. No. | Alk^a | Y | Alk^b | L | Physical data |
|---|---|---|---|---|---|---|
| 106 | B2 | cb | C=O | —CH$_2$— | 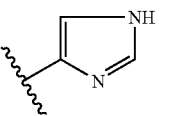 | 2R-trans |
| 107 | B3b | cb | C=O | —CH$_2$— | 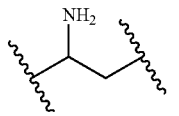 | 2R-trans |
| 13 | B8 | cb | C=O | 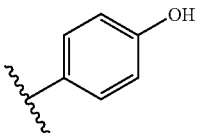 | 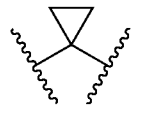 | 2R-trans, HCl(1:3); H$_2$O(1:1) |
| 108 | B2 | cb | C=O | 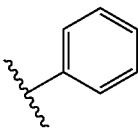 | 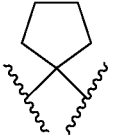 | 2R-trans HCl(1:2) H$_2$O(1:1) |
| 109 | B2 | cb | C=O | 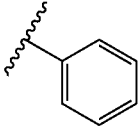 | 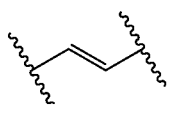 | 2R-trans |
| 110 | B3b | cb | C=O | 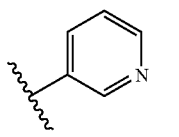 | 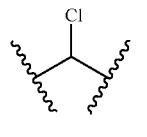 | [2R-[2α,4β(E)]] |
| 111 | B2 | cb | C=O | 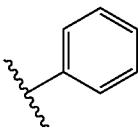 |  | 2R-trans |

TABLE 1-continued
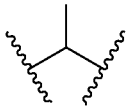
| Comp. No. | Exp. No. | Alk$^a$ | Y | Alk$^b$ | L | Physical data |
|---|---|---|---|---|---|---|
| 112 | B2 | cb | C=O | 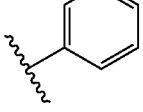 | 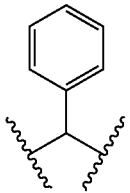 | 2R-trans |
| 152 | B4c | cb | C=O | 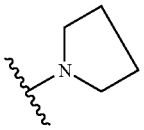 | 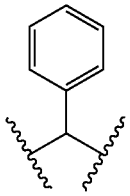 | B-trans |
| 113 | B4c | cb | C=O | 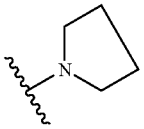 | 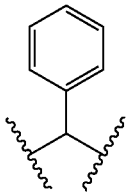 | B-trans HCl(1:3) H$_2$O(1:3) |
| 114 | B4b | cb | C=O | 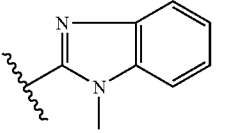 | 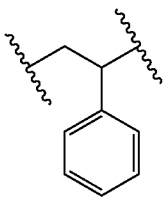 | B-trans |
| 115 | B3b | cb | C=O | 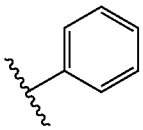 | 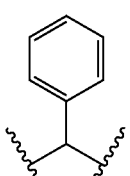 | B-trans |
| 116 | B4c | cb | C=O | 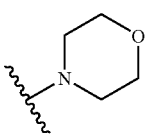 | | 2R-trans |

TABLE 1-continued

| Comp. No. | Exp. No. | Alk^a | Y | Alk^b | L | Physical data |
|---|---|---|---|---|---|---|
| 6 | B4a | -CH(Ph)- (benzyl-substituted methylene) | C=O | cb | morpholin-4-yl | 2R-trans |
| 117 | B2 | -CH₂CH₂CH₂- (propylene) | C=O | cb | -OCH₃ | 2R-trans |
| 168 | B2 | cb | O=S=O | cb | phenyl | 2R-trans |
| 118 | B2 | cb | O=S=O | cb | 3,5-bis(trifluoromethyl)phenyl | B-trans |
| 119 | B2 | cb | O=S=O | cb | 2-methoxy-5-methylphenyl | B-trans | cb = Covalent Bond

TABLE 2
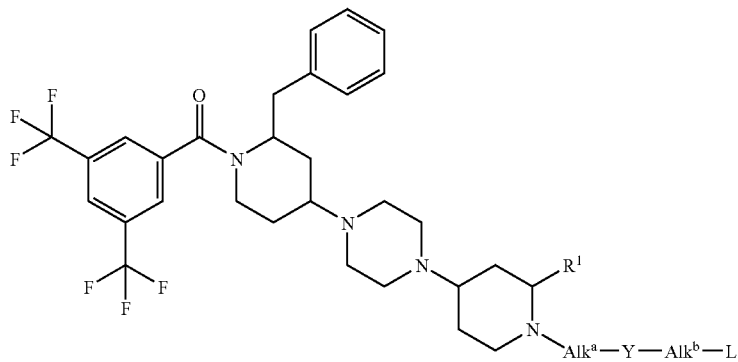
| Co No. | Exp. No. | R¹ | Alkᵃ | Y | Alkᵇ | L | Physical data |
|---|---|---|---|---|---|---|---|
| 10 | B6 | benzyl | cb | C=O | cb | 3,5-dimethylphenyl | [2α,4α(2R*,4S*)] |
| 11 | B6 | benzyl | cb | C=O | cb | 3,5-dimethylphenyl | [2α,4β(2R*,4S*)] |
cb = Covalent Bond
TABLE 3
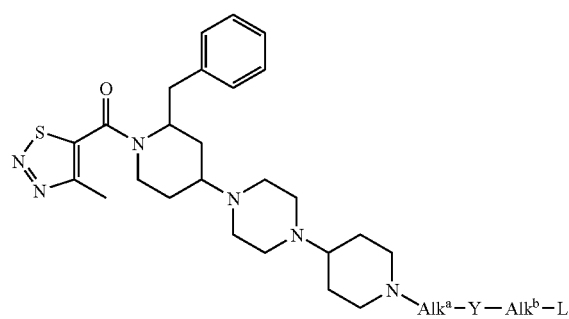
| Co No. | Exp. No. | Alkᵃ | Y | Alkᵇ | L | Physical data |
|---|---|---|---|---|---|---|
| 153 | B15 | cb | C=O | cb | 4-methyl-1,2,3-thiadiazol-5-yl | 2R-trans |
cb = Covalent Bond
TABLE 4
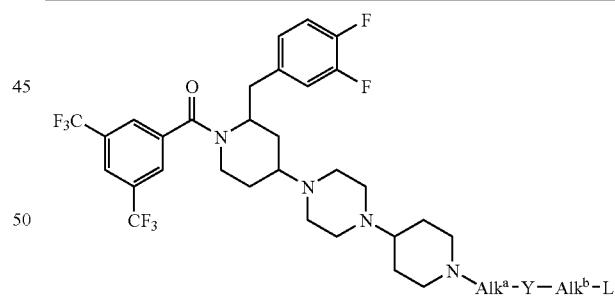
| Co No. | Exp No. | Alkᵃ | Y | Alkᵇ | L | Physical data |
|---|---|---|---|---|---|---|
| 154 | B1a | —CH₂— | cb | cb | phenyl | 2R-cis |
| 155 | B1a | —CH₂— | cb | cb | phenyl | 2R-trans |

TABLE 4-continued

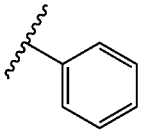

| Co No. | Exp No. | Alk$^a$ | Y | Alk$^b$ | L | Physical data |
|---|---|---|---|---|---|---|
| 156 | B1b | cb | cb | cb | —H | 2R-trans |
| 157 | B2 | cb | C=O | cb | 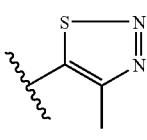 | 2R-trans |
| 158 | B2 | cb | C=O | cb | 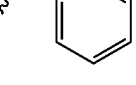 | 2R-trans | cb = Covalent Bond

TABLE 5

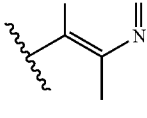

| Co No. | Exp No. | Alk$^a$ | Y | Alk$^b$ | L | Physical data |
|---|---|---|---|---|---|---|
| 175 | B1b | cb | cb | cb | H | cis |
| 174 | B1a | —CH$_2$— | cb | cb | | cis |
| 176 | B2 | cb | C=O | cb | 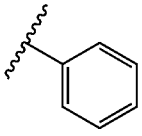 | cis |
| 177 | B2 | cb | C=O | cb | | cis |

C. PHARMACOLOGICAL EXAMPLE

Example C.1

Binding Experiment for h-NK1, h-NK2 and h-NK3 Receptors

The compounds according to the invention were investigated for interaction with various neurotransmitter receptors, ion channels and transporter binding sites using the radioligand binding technique. Membranes from tissue homogenates or from cells, expressing the receptor or transporter of interests, were incubated with a radioactively labelled substance ([$^3$H]- or [$^{125}$I] ligand) to label a particular receptor. Specific receptor binding of the radioligand was distinguished from the non-specific membrane labelling by selectively inhibiting the receptor labelling with an unlabelled drug (the blank), known to compete with the radioligand for binding to the receptor sites. Following incubation, labelled membranes were harvested and rinsed with excessive cold buffer to remove non-bound radioactivity by rapid filtration under suction. Membrane bound radioactivity was counted in a scintillation counter and results were expressed in counts per minute (cpm).

The compounds were dissolved in DMSO and tested at 10 concentrations ranging from $10^{-10}$ to $10^{-5}$ M.

The ability of the compounds according to the invention to displace [$^3$H]-Substance P from cloned human h-NK$_1$ receptors expressed in CHO cells, to displace [$^3$H]-SR-48968 from cloned human h-NK$_2$ receptors expressed in Sf9 cells, and to displace [$^3$H]-SR-142801 from cloned human h-NK$_3$ receptors expressed in CHO cells was evaluated.

The pIC$_{5-0}$ data for the h-NK$_1$, h-NK$_2$ and h-NK$_3$ receptor testing for a representative selection of compounds are presented in Table 3.

All selected compounds show (sub)nanomolar affinity for the h-NK$_1$ receptor most of them with more than 100-fold selectivity towards the h-NK$_2$ and h-NK$_3$ receptors.

Example C.2

Signal Transduction

This test evaluates in vitro functional NK$_1$ antagonistic activity. For the measurements of intracellular Ca$^{++}$ concentrations the cells were grown on 96-well (black wall/transparent bottom) plates from Costar for 2 days until they reached confluence. The cells were loaded with 2 μM Fluo3 in DMEM containing 0.1% BSA and 2.5 mM probenecid for 1 h at 37° C. They were washed 3× with a Krebs buffer (140 mM NaCl, 1 mM MgCl$_2$x6H$_2$O, 5 mM KCl, 10 mM glucose, 5 mM HEPES; 1.25 mM CaCl$_2$; pH 7.4) containing 2.5 mM probenecid and 0.1% BSA (Ca$^{++}$-buffer). The cells were preincubated with a concentration range of antagonists for 20 min at RT and Ca$^{++}$-signals after addition of the agonists were measured in a Fluorescence Image Plate Reader (FLIPR from Molecular Devices, Crawley, England). The peak of the Ca$^{++}$-transient was considered as the relevant signal and the mean values of corresponding wells were analysed as described below.

The sigmoidal dose response curves were analysed by computerised curve-fitting, using the GraphPad Program. The EC$_{50}$-value of a compound is the effective dose showing 50% of maximal effect. For mean curves the response to the agonist with the highest potency was normalised to 100%. For antagonist responses the IC$_{50}$-value was calculated using non-linear regression.

TABLE

| Co No. | h-NK$_1$ pIC$_{50}$ | h-NK$_2$ pIC$_{50}$ | h-NK$_3$ pIC$_{50}$ |
|---|---|---|---|
| 2 | 8.6 | 5.8 | 5.2 |
| 3 | 8.9 | 6.3 | 6.6 |
| 4 | 8.8 | 5.2 | 6.7 |
| 5 | 10.0 | 6.1 | 6.3 |
| 6 | 9.0 | — | — |
| 7 | 8.1 | 6.0 | 6.0 |
| 8 | 9.2 | — | — |
| 9 | 8.9 | 6.2 | 6.3 |
| 10 | 7.3 | 6.4 | 6.2 |
| 11 | 7.4 | 6.2 | 6.6 |
| 12 | 9.1 | 6.0 | 6.1 |
| 13 | 8.9 | 6.2 | 6.0 |
| 16 | 9.0 | 6.3 | 6.8 |
| 22 | 9.4 | 6.2 | 6.5 |
| 26 | 7.4 | 6.0 | 6.0 |
| 32 | 8.8 | 6.2 | 6.8 |
| 36 | 9.0 | 6.1 | 6.1 |
| 37 | 8.4 | 6.3 | 6.6 |
| 39 | 9.1 | 6.0 | 6.0 |
| 42 | 8.6 | — | — |
| 45 | 9.5 | — | — |
| 51 | 8.9 | 6.2 | 6.4 |
| 56 | 9.0 | 6.3 | 6.7 |
| 62 | 9.2 | 6.4 | 6.6 |
| 64 | 8.1 | 6.4 | 6.4 |
| 65 | 8.4 | 6.2 | 6.6 |
| 77 | 9.0 | 6.1 | 5.6 |
| 78 | 9.1 | 6.4 | 6.0 |
| 79 | 8.2 | 6.5 | 6.4 |
| 80 | 9.3 | 6.1 | 6.6 |
| 85 | 8.5 | — | — |
| 89 | 8.6 | 6.2 | 6.2 |
| 90 | 7.5 | 6.5 | 6.9 |
| 97 | 9.5 | 6.3 | 6.4 |
| 102 | 9.0 | — | — |
| 104 | 9.2 | 5.8 | 5.8 |
| 106 | 9.0 | 6.0 | 6.3 |
| 108 | 8.8 | — | — |
| 110 | 10.0 | — | — |
| 113 | 9.0 | 6.4 | 6.4 |
| 116 | 8.6 | 6.1 | 6.8 |
| 119 | 7.6 | 6.0 | 6.0 |
| 132 | 8.0 | 5.7 | 5.5 |
| 133 | 8.4 | 5.9 | 6.1 |
| 134 | 7.7 | 5.6 | <5 |
| 139 | 8.8 | 6.1 | 6.5 |
| 140 | 8.5 | 5.4 | 5.3 |
| 141 | 8.1 | 5.4 | 5.4 |
| 142 | 8.9 | 6.2 | 6.6 |
| 143 | 9.0 | 6.1 | 6.3 |
| 144 | ? | 5.9 | 6.2 |
| 151 | 9.4 | 6.2 | 6.4 |

D. COMPOSITION EXAMPLES

"Active ingredient" (A.I.) as used throughout these examples relates to a compound of Formula (I), the pharmaceutically acceptable acid or base addition salts thereof, the stereochemically isomeric forms thereof, the N-oxide form thereof and prodrugs thereof.

Example D.1

Oral Drops

500 Grams of the A.I. was dissolved in 0.5 l of 2-hydroxypropanoic acid and 1.5 l of the polyethylene glycol at 60~80° C. After cooling to 30~40° C. there were added 35 l of polyethylene glycol and the mixture was stirred well. Then there was added a solution of 1750 grams of sodium saccharin in 2.5 l of purified water and while stirring there were added 2.5 l of cocoa flavor and polyethylene glycol q.s. to a volume of 50 l, providing an oral drop solution comprising 10 mg/ml of A.I. The resulting solution was filled into suitable containers.

Example D.2

Oral Solution

9 Grams of methyl 4-hydroxybenzoate and 1 gram of propyl 4-hydroxybenzoate were dissolved in 4 l of boiling purified water. In 3 l of this solution were dissolved first 10 grams of 2,3-dihydroxybutanedioic acid and thereafter 20 grams of the A.I. The latter solution was combined with the remaining part of the former solution and 12 l 1,2,3-propanetriol and 3 l of sorbitol 70% solution were added thereto. 40 Grams of sodium saccharin were dissolved in 0.5 l of water and 2 ml of raspberry and 2 ml of gooseberry essence were added. The latter solution was combined with the former, water was added q.s. to a volume of 20 l providing an oral solution comprising 5 mg of the active ingredient per teaspoonful (5 ml). The resulting solution was filled in suitable containers.

Example D.3

Film-Coated Tablets

Preparation of Table Core

A mixture of 100 grams of the A.I., 570 grams lactose and 200 grams starch was mixed well and thereafter humidified with a solution of 5 grams sodium dodecyl sulfate and 10 grams polyvinylpyrrolidone in about 200 ml of water. The wet powder mixture was sieved, dried and sieved again. Then there was added 100 grams microcrystalline cellulose and 15 grams hydrogenated vegetable oil. The whole was mixed well and compressed into tablets, giving 10.000 tablets, each containing 10 mg of the active ingredient.

Coating

To a solution of 10 grams methyl cellulose in 75 ml of denaturated ethanol there was added a solution of 5 grams of ethyl cellulose in 150 ml of dichloromethane. Then there were added 75 ml of dichloromethane and 2.5 ml 1,2,3-propanetriol. 10 Grams of polyethylene glycol was molten and dissolved in 75 ml of dichloromethane. The latter solution was added to the former and then there were added 2.5 grams of magnesium octadecanoate, 5 grams of polyvinylpyrrolidone and 30 ml of concentrated color suspension and the whole was homogenated. The tablet cores were coated with the thus obtained mixture in a coating apparatus.

Example D.4

Injectable Solution 1.8 Grams methyl 4-hydroxybenzoate and 0.2 grams propyl 4-hydroxybenzoate were dissolved in about 0.5 l of boiling water for injection. After cooling to about 50° C. there were added while stirring 4 grams lactic acid, 0.05 grams propylene glycol and 4 grams of the A.I. The solution was cooled to room temperature and supplemented with water for injection q.s. ad 1 l, giving a solution comprising 4 mg/ml of A.I. The solution was sterilized by filtration and filled in sterile containers.

The invention claimed is:

1. A compound according to the general Formula (I)

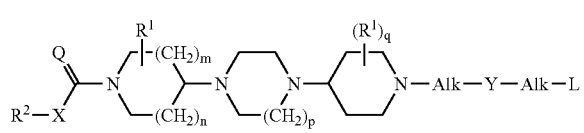

the pharmaceutically acceptable acid or base addition salts thereof, the stereochemically isomeric forms thereof, wherein:

n is an integer equal to 1;
m is an integer equal to 1;
p is an integer equal to 1;
Q is O or $NR^3$;
X is a covalent bond or a radical of formula —O—, —S— or —$NR^3$—;
each $R^3$ independently from each other, is hydrogen or alkyl;
each $R^1$ independently from each other, is selected from the group consisting of $Ar^1$, $Ar^1$-alkyl and di($Ar^1$)-alkyl;
q is an integer equal to 0 or 1;
$R^2$ is selected from the group consisting of alkyl, $Ar^2$, $Ar^2$-alkyl, $Het^1$ or $Het^1$-alkyl;
Y is a covalent bond or a bivalent radical of formula —C(=O)— or —$SO_2$—;
each Alk represents, independently from each other, a covalent bond; a bivalent straight or branched, saturated or unsaturated hydrocarbon radical having from 1 to 6 carbon atoms; or a cyclic saturated or unsaturated hydrocarbon radical having from 3 to 6 carbon atoms; each radical optionally substituted on one or more carbon atoms with one or more alkyl, phenyl, halo, cyano, hydroxy, formyl and amino radicals;
L is selected from the group of hydrogen, alkyloxy, $Ar^3$-oxy, alkyloxycarbonyl, mono- and di(alkyl)amino, mono- and di($Ar^3$)amino, mono- and di(alkyloxycarbonyl)amino, $Ar^3$, $Ar^3$-carbonyl, $Het^2$ and $Het^2$-carbonyl;
$Ar^1$ is phenyl, optionally substituted with 1, 2 or 3 substituents each independently from each other selected from the group consisting of halo, alkyl, cyano, aminocarbonyl and alkyloxy;
$Ar^2$ is naphthalenyl or phenyl, each optionally substituted with 1, 2 or 3 substituents, each independently from each other, selected from the group consisting of halo, nitro, amino, mono- and di(alkyl)amino, cyano, alkyl, hydroxy, alkyloxy, carboxyl, alkyloxycarbonyl, aminocarbonyl and mono- and di(alkyl)aminocarbonyl;
$Ar^3$ is naphthalenyl or phenyl, optionally substituted with 1, 2 or 3 substituents each independently from each other selected from the group consisting of alkyloxy, alkyl, halo, hydroxy, pyridinyl, morpholinyl, pyrrolidinyl, imidazo[1,2-α]pyridinyl, morpholinylcarbonyl, pyrrolidinylcarbonyl, amino and cyano;
$Het^1$ is a monocyclic heterocyclic radical selected from the group consisting of pyrrolyl, pyrazolyl, imidazolyl, furanyl, thienyl, oxazolyl, isoxazolyl, thiazolyl, thiadiazolyl, isothiazolyl, pyridinyl, pyrimidinyl, pyrazinyl and pyridazinyl; or a bicyclic heterocyclic radical selected from the group of quinolinyl, quinoxalinyl, indolyl, benzimidazolyl, benzoxazolyl, benzisoxazolyl, benzothiazolyl, benzisothiazolyl, benzofuranyl and benzothienyl;
each heterocyclic radical may optionally be substituted on any atom by a radical selected from the group consisting of halo and alkyl;
$Het^2$ is a monocyclic heterocyclic radical selected from the group consisting of pyrrolidinyl, dioxolyl, imidazolidinyl, pyrrazolidinyl, piperidinyl, morpholinyl, dithianyl, thiomorpholinyl, piperazinyl, imidazolidinyl, tetrahydrofuranyl, 2H-pyrrolyl, pyrrolinyl, imidazolinyl, pyrrazolinyl, pyrrolyl, imidazolyl, pyrazolyl, triazolyl, furanyl, thienyl, oxazolyl, isoxazolyl, thiazolyl, thiadiazolyl, isothiazolyl, pyridinyl, pyrimidinyl, pyrazinyl, pyridazinyl and triazinyl; or a bicyclic heterocyclic radical selected from the group consisting of benzopiperidinyl, quinolinyl, quinoxalinyl, indolyl, isoindolyl, chromenyl, benzimidazolyl, imidazo[1,2-α]pyridinyl, benzoxazolyl, benzisoxazolyl, benzothiazolyl, benzisothiazolyl, benzofuranyl and benzothienyl; each radical optionally substituted with one or more radicals selected from the group consisting of $Ar^1$, $Ar^1$alkyl, halo, hydroxy, alkyl, piperidinyl, pyrrolyl, thienyl, oxo, alkyloxy, alkyloxyalkyl and alkyloxycarbonyl; and
alkyl is a straight or branched saturated hydrocarbon radical having from 1 to 6 carbon atoms or a cyclic saturated hydrocarbon radicals having from 3 to 6 carbon atoms; optionally substituted on one or more carbon atoms with one or more radicals selected from the group consisting of phenyl, halo, cyano, oxo, hydroxy, formyl and amino radicals.

2. The compound according to claim 1, wherein the compound of Formula I is {4-[4-(1-benzoylpiperidin-4-yl)-piperazin-1-yl]-2-benzyl-piperidin-1-yl}-(3,5-bistrifluoromethylphenyl)methanone:

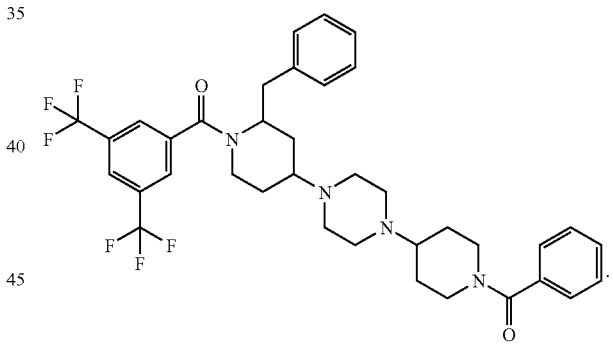

3. The compound according to claim 1, characterized wherein

Q is O;
X is a covalent bond;
each $R^1$ is $Ar^1$ or $Ar^1$-alkyl;
q is 0 or 1;
$R^2$ is $Ar^2$;
Y is a covalent bond or a bivalent radical of formula —C(=O)— or —$SO_2$—;
each Alk represents, independently from each other, a covalent bond; a bivalent straight or branched, saturated or unsaturated hydrocarbon radical having from 1 to 6 carbon atoms; or a cyclic saturated or unsaturated hydrocarbon radical having from 3 to 6 carbon atoms; each radical optionally substituted on one or more carbon atoms with one or more phenyl, halo, cyano, hydroxy, formyl and amino radicals;

L is selected from the group of hydrogen, alkyloxy, $Ar^3$-oxy, alkyloxy-carbonyl, mono- and di(alkyl)amino, mono-and di($Ar^3$)amino, $Ar^3$ and $Het^2$;

$Ar^1$ is phenyl, optionally substituted with 1, 2 or 3 alkyl radicals;

$Ar^2$ is phenyl, optionally substituted with 1, 2 or 3 alkyl radicals;

$Ar^3$ is phenyl, optionally substituted with 1, 2 or 3 substituents each independently from each other selected from the group of alkyloxy, alkyl, halo, hydroxy, pyridinyl, morpholinyl, pyrrolidinyl, imidazo[1,2-α]pyridinyl, morpholinylcarbonyl, pyrrolidinylcarbonyl, amino and cyano;

$Het^2$ is a monocyclic heterocyclic radical selected from the group of pyrrolidinyl, piperidinyl, morpholinyl, pyrrolyl, imidazolyl, pyrazolyl, furanyl, thienyl, isoxazolyl, thiazolyl, thiadiazolyl, pyridinyl, pyrimidinyl, pyrazinyl, and pyridazinyl; or a bicyclic heterocyclic radical selected from the group of benzopiperidinyl, quinolinyl, quinoxalinyl, indolyl, chromenyl and benzimidazolyl; each radical optionally substituted with one or more radicals selected from the group of $Ar^1$, $Ar^1$alkyl, halo, hydroxy, alkyl, piperidinyl, pyrrolyl, thienyl, oxo and alkyloxycarbonyl; and alkyl is a straight hydrocarbon radical having 1 to 6 carbon atoms, optionally substituted with one or more halo radicals.

4. The compound according to claim 1, wherein $R^1$ is $Ar^1$methyl and attached to the 2-position or $R^1$ $Ar^1$ and attached to the 3-position.

5. The compound according to claim 1, wherein the $R^2$—X—C(=Q)- moiety is 3,5-di-(trifluoromethyl) phenylcarbonyl.

6. A pharmaceutical composition comprising a pharmaceutically acceptable carrier and, as active ingredient, a therapeutically effective amount of a compound according to claim 1.

7. The pharmaceutical composition according to claim 6, wherein the pharmaceutical composition is an oral dosage form suitable to be orally administered.

8. A process for the preparation of a composition as claimed in claim 1, wherein a pharmaceutically acceptable carrier is intimately mixed with a therapeutically effective amount of a compound as claimed in claim 1.

9. A process for the preparation of a compound of claim 1, wherein a) a final compound of Formula (I) is obtained by reductive N-alkylation of an intermediate of Formula (II) wherein $R^1$, $R^2$, X, Q, m, n and p are defined as in claim 1, with an N-substituted piperdinone of Formula (III) wherein $R^1$, Alk, Y, L and q are defined as in claim 1, in a reaction-inert solvent and in the presence of a reducing agent; or

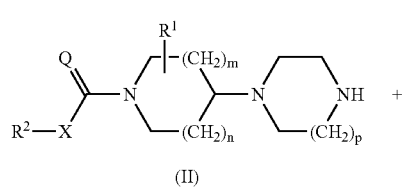

(II)

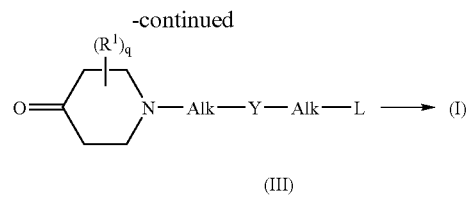

b) a final compound of Formula ($I^a$) is obtained by acylation of a final compound of Formula (I') wherein $R^1$, $R^2$, X, Q, m, n, p and q are defined as in claim 1, with an acyl compound of Formula (V) wherein Alk and L are defined as in claim 1 and $W^1$ is a leaving group, in a reaction-inert solvent and in the presence of a base; or

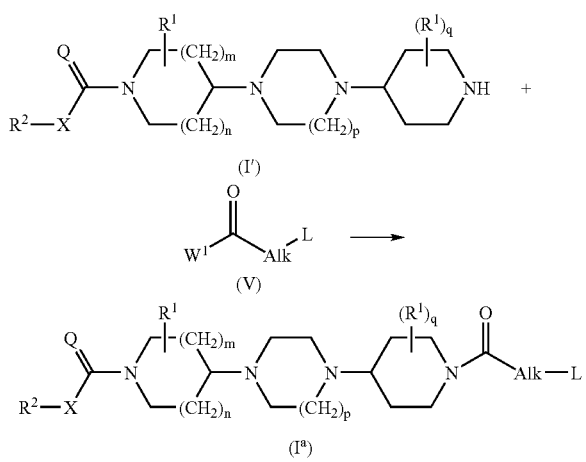

c) a final compound of Formula ($I^a$) is obtained by a base-catalyzed nucleophilic addition reaction of a final compound of Formula (I') wherein $R^1$, $R^2$, X, Q, m, n, p and q are defined as in claim 1, with a carboxylic acid of Formula (VI) wherein Alk and L are defined as in claim 1, or its ester, in a reaction-inert solvent and in the presence of a base; or

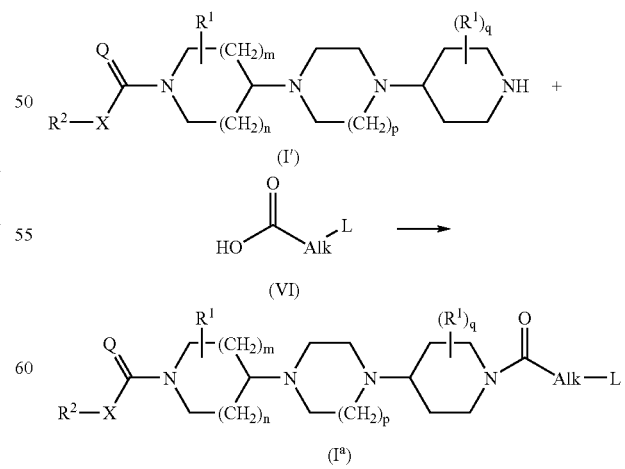

d) a final compound of Formula ($I^b$) is obtained by a base-catalyzed nucleophilic addition reaction of a final compound of Formula (I') wherein $R^1$, $R^2$, X, Q, m, n, p and q are defined as in claim 1, with a compound of Formula (VII) wherein Alk and L are defined as in claim 1 and $W^2$ is a leaving group, in a reaction-inert solvent and in the presence of a base; or

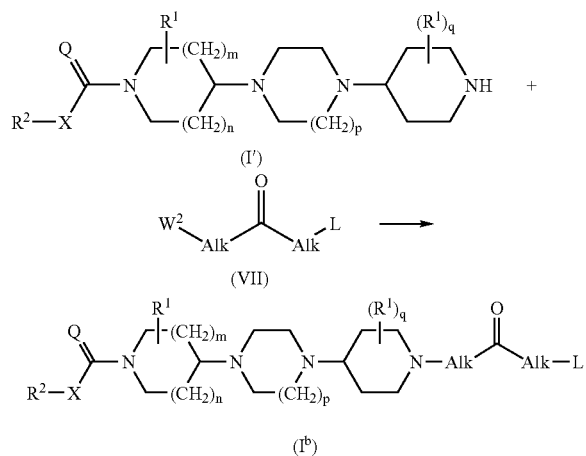

e) a final compound of Formula ($I^c$) is obtained by reductive amination/alkylation of a final compound of Formula (I') wherein $R^1$, $R^2$, X, Q, m, n, p and q are defined as in claim 1 with a compound of Formula (VIII) wherein Alk and L are defined as in claim 1 and $W^3$ is a leaving group, in a reaction-inert solvent and in the presence of a base; and

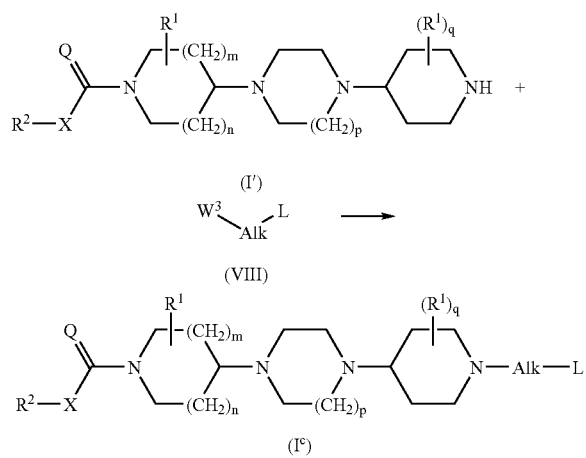

f) optionally converting a compound of claim 1 into an acid addition salt by treatment with an acid, or into a base addition salt by treatment with a base, or conversely, converting an acid addition salt form into the free base by treatment with alkali, or converting a base addition salt into the free acid by treatment with an acid; or preparing the N-oxide and/or steroechemically isomeric forms thereof.

10. A process for the preparation of a compound of Formula (XIII), wherein a compound of Formula (XI), wherein A is an aryl or heteroaryl, Z is $Z^1$ as defined below wherein each variable is defined as in claim 1, Hal is an halogen and r is an integer ranging from 1 to a number equal to the number of available carbon atoms in the aryl or heteroaryl-moiety A, is reacted with an unsaturated heteroaryl Het of Formula (XII) in the presence of catalytic amounts of Pd(OAc)$_2$ and 1,3-bis diphenylphosphinopropane, in the presence of a suitable base, preferably Cs$_2$CO$_3$ or K(AcO) and in a reaction-inert polar solvent.

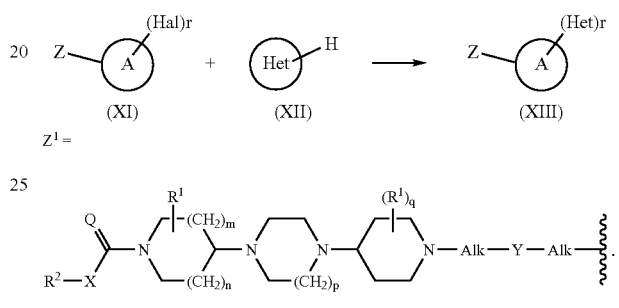

11. The process according to claim 10, wherein Hal is bromo or iodo, A is phenyl or pyridinyl, Z is $Z^1$ and Het imidazo[1,2-α]pyridinyl, pyrrolyl or thienyl.

12. A method of treating a warm-blooded animal suffering from emesis, depression, anxiety disorder, pain, pancreatitis, micturition disorder, or iffitable bowel syndrome comprising administering to said animal a therapeutically effect amount of a compound according to claim 1.

13. The method of claim 12, wherein the micturition disorder is overactive bladder.

14. The method of claim 12, wherein the animal suffers from emesis.

15. The method of claim 12, wherein the animal suffers from depression.

16. The method of claim 12, wherein the animal suffers from anxiety disorder.

17. The method of claim 12, wherein the animal suffers from pain.

18. The method of claim 12, wherein the animal suffers from pancreatitis.

19. The method of claim 12, wherein the animal suffers from micturition disorder.

20. The method of claim 12, wherein the animal suffers from irritable bowel syndrome.

* * * * *

UNITED STATES PATENT AND TRADEMARK OFFICE
CERTIFICATE OF CORRECTION

PATENT NO. : 7,410,970 B2  Page 1 of 1
APPLICATION NO. : 10/527821
DATED : August 12, 2008
INVENTOR(S) : Frans Eduard Janssens et al.

It is certified that error appears in the above-identified patent and that said Letters Patent is hereby corrected as shown below:

Column 91,
Claim 1, line 14, delete "thereof," and insert -- thereof and --.

Column 93,
Claim 4, line 32, delete "$R^1$ $Ar^1$" and insert -- $R^1$ is $Ar^1$ --.

Column 96,
Claim 12, line 36, delete "iffitable" and insert -- irritable --.

Signed and Sealed this

Twenty-second Day of December, 2009

David J. Kappos
*Director of the United States Patent and Trademark Office*